United States Patent
Hoffman et al.

(10) Patent No.: US 10,595,832 B2
(45) Date of Patent: Mar. 24, 2020

(54) DEVICE FOR VISUALIZING REAL-TIME SAMPLING

(71) Applicant: Spiration, Inc., Redmond, WA (US)

(72) Inventors: Peter Hoffman, Seattle, WA (US); David H. Dillard, Grapeview, WA (US); Hugo X. Gonzalez, Woodinville, WA (US); Desmond O'Connell, Lake Forest Park, WA (US)

(73) Assignee: Spiration, Inc., Redmond, WA (US)

( * ) Notice: Subject to any disclaimer, the term of this patent is extended or adjusted under 35 U.S.C. 154(b) by 514 days.

(21) Appl. No.: 15/402,544

(22) Filed: Jan. 10, 2017

(65) Prior Publication Data

US 2017/0143317 A1    May 25, 2017

Related U.S. Application Data

(63) Continuation of application No. 14/199,245, filed on Mar. 6, 2014, now abandoned.

(Continued)

(51) Int. Cl.
*A61B 10/04* (2006.01)
*A61B 17/34* (2006.01)
(Continued)

(52) U.S. Cl.
CPC .............. *A61B 10/04* (2013.01); *A61B 1/018* (2013.01); *A61B 1/2676* (2013.01); *A61B 8/0841* (2013.01); *A61B 8/12* (2013.01); *A61B 8/445* (2013.01); *A61B 10/0233* (2013.01); *A61B 10/0266* (2013.01); *A61B 17/3417* (2013.01); *A61B 2010/045* (2013.01); *A61B 2018/00023* (2013.01); *A61B 2018/00095* (2013.01); *A61B 2018/00208* (2013.01); *A61B 2018/00541* (2013.01); *A61B 2018/00577* (2013.01);
(Continued)

(58) Field of Classification Search
CPC . A61B 10/04; A61B 10/0233; A61B 10/0266; A61B 1/018; A61B 1/008; A61B 1/01; A61B 1/2676; A61B 17/3417; A61B 2090/3782
See application file for complete search history.

(56) References Cited

U.S. PATENT DOCUMENTS

| | | |
|---|---|---|
| 4,766,906 A | 8/1988 | Wang |
| 5,419,777 A | 5/1995 | Hofling |

(Continued)

FOREIGN PATENT DOCUMENTS

| | | |
|---|---|---|
| EP | 1830714 B1 | 7/2012 |
| JP | 2011125389 A | 6/2011 |

(Continued)

OTHER PUBLICATIONS

International Search Report for PCT Application No. PCT/US2014/021470.

*Primary Examiner* — Carolyn A Pehlke

(57) ABSTRACT

Systems, methods, and devices for providing real-time imaging of tissue sampling. An ultrasound probe is received with a first lumen of a catheter and a tissue sampling device is received with a second lumen of the catheter. The catheter is received within a working channel of a bronchoscope. The ultrasound probe is a radial ultrasound probe that generates real-time ultrasound images of the tissue sampling device and surrounding tissue.

14 Claims, 25 Drawing Sheets

Related U.S. Application Data

(60) Provisional application No. 61/779,483, filed on Mar. 13, 2013.

(51) Int. Cl.
| | |
|---|---|
| *A61B 10/02* | (2006.01) |
| *A61B 8/08* | (2006.01) |
| *A61B 1/018* | (2006.01) |
| *A61B 1/267* | (2006.01) |
| *A61B 8/12* | (2006.01) |
| *A61B 8/00* | (2006.01) |
| *A61B 18/00* | (2006.01) |
| *A61B 18/04* | (2006.01) |
| *A61M 25/00* | (2006.01) |
| *A61B 90/00* | (2016.01) |

(52) U.S. Cl.
CPC ............ *A61B 2018/00595* (2013.01); *A61B 2018/00982* (2013.01); *A61B 2018/046* (2013.01); *A61B 2090/376* (2016.02); *A61B 2090/3966* (2016.02); *A61M 2025/0087* (2013.01); *A61M 2025/0089* (2013.01)

(56) References Cited

U.S. PATENT DOCUMENTS

| | | | |
|---|---|---|---|
| 5,469,853 A * | 11/1995 | Law | A61B 8/0833 600/463 |
| 5,910,150 A | 6/1999 | Saadat | |
| 6,283,951 B1 | 9/2001 | Flaherty | |
| 6,749,560 B1 | 6/2004 | Konstorum | |
| 6,793,633 B2 | 9/2004 | Douglas | |
| 7,320,683 B2 | 1/2008 | Prais | |
| 8,273,062 B2 | 9/2012 | Villette | |
| 8,328,772 B2 | 12/2012 | Kinast | |
| 2001/0037808 A1* | 11/2001 | Deem | A61B 17/12022 128/200.24 |
| 2002/0026188 A1 | 2/2002 | Balbierz | |
| 2002/0095124 A1 | 7/2002 | Palasis | |
| 2003/0045778 A1* | 3/2003 | Ohline | A61B 1/0053 600/114 |
| 2003/0208136 A1 | 11/2003 | Mark | |
| 2004/0064098 A1 | 4/2004 | Cuschieri | |
| 2006/0149129 A1* | 7/2006 | Watts | A61B 1/00135 600/113 |
| 2009/0131950 A1 | 5/2009 | Liu | |
| 2010/0069786 A1 | 3/2010 | Globerman | |
| 2010/0312141 A1* | 12/2010 | Keast | A61B 10/0266 600/567 |
| 2010/0331618 A1 | 12/2010 | Galperin | |
| 2011/0282368 A1 | 11/2011 | Swayze | |
| 2013/0225997 A1 | 8/2013 | Dillard et al. | |

FOREIGN PATENT DOCUMENTS

| | | |
|---|---|---|
| JP | 2011125632 A | 6/2011 |
| JP | 2013116288 A | 6/2011 |

* cited by examiner

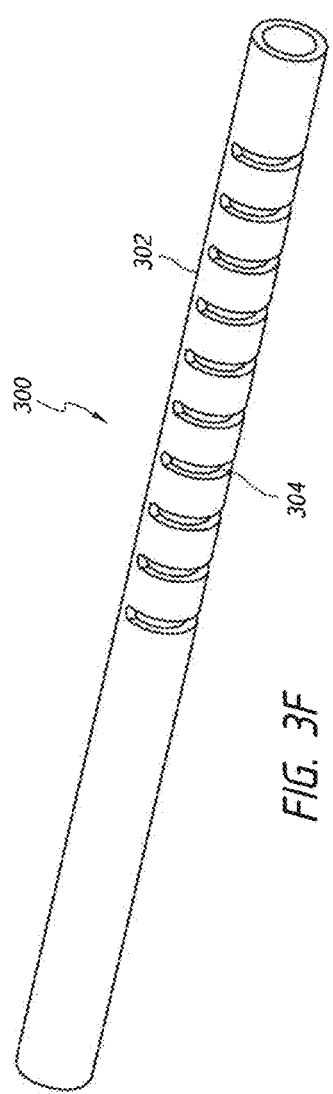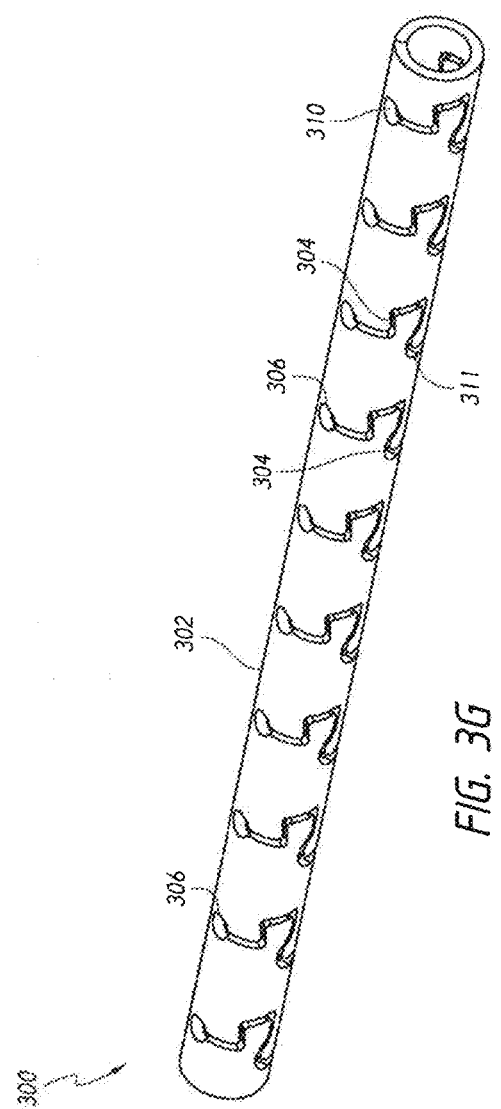
FIG. 3F
FIG. 3G

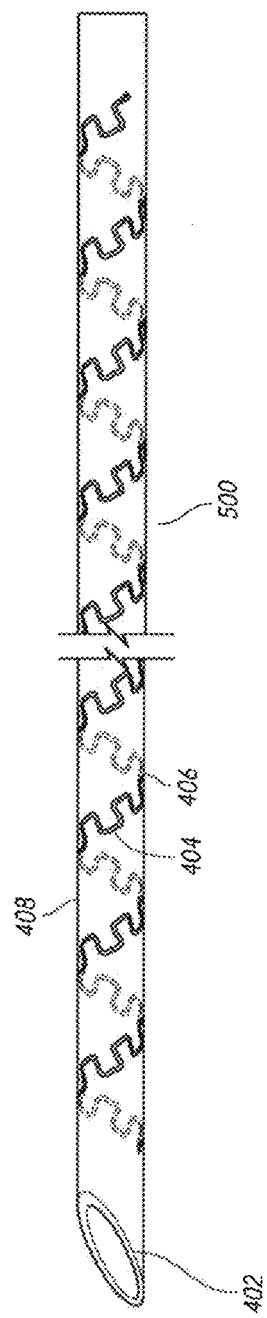

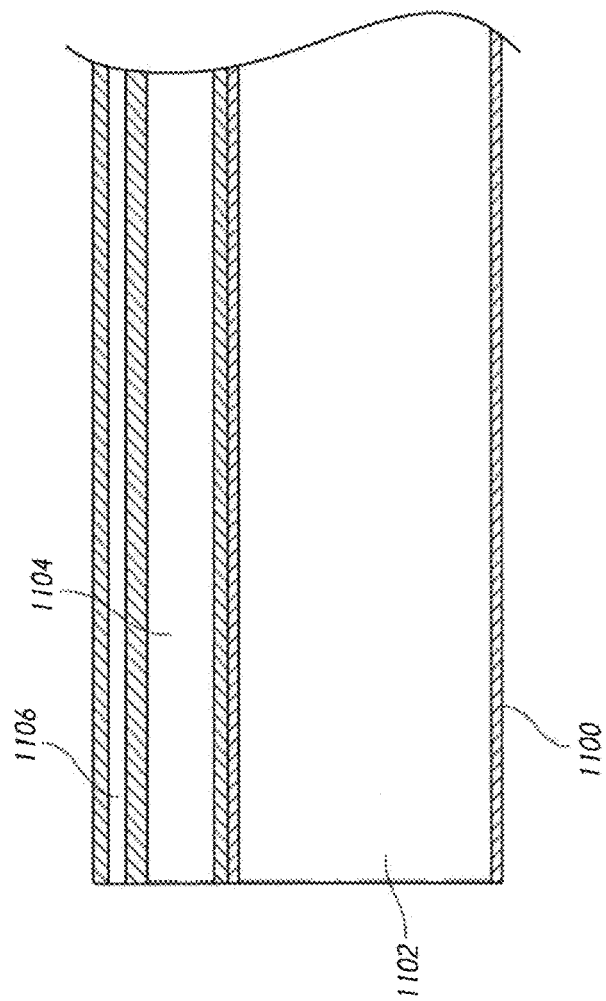
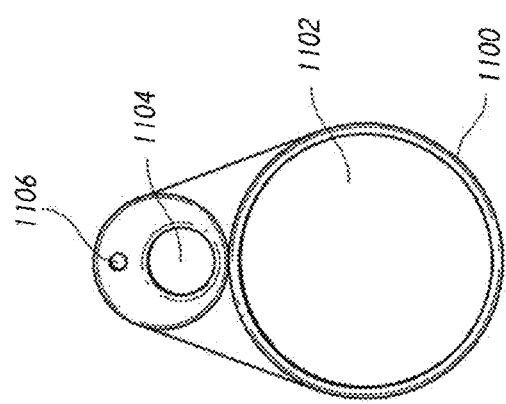
FIG. 11B
FIG. 11A

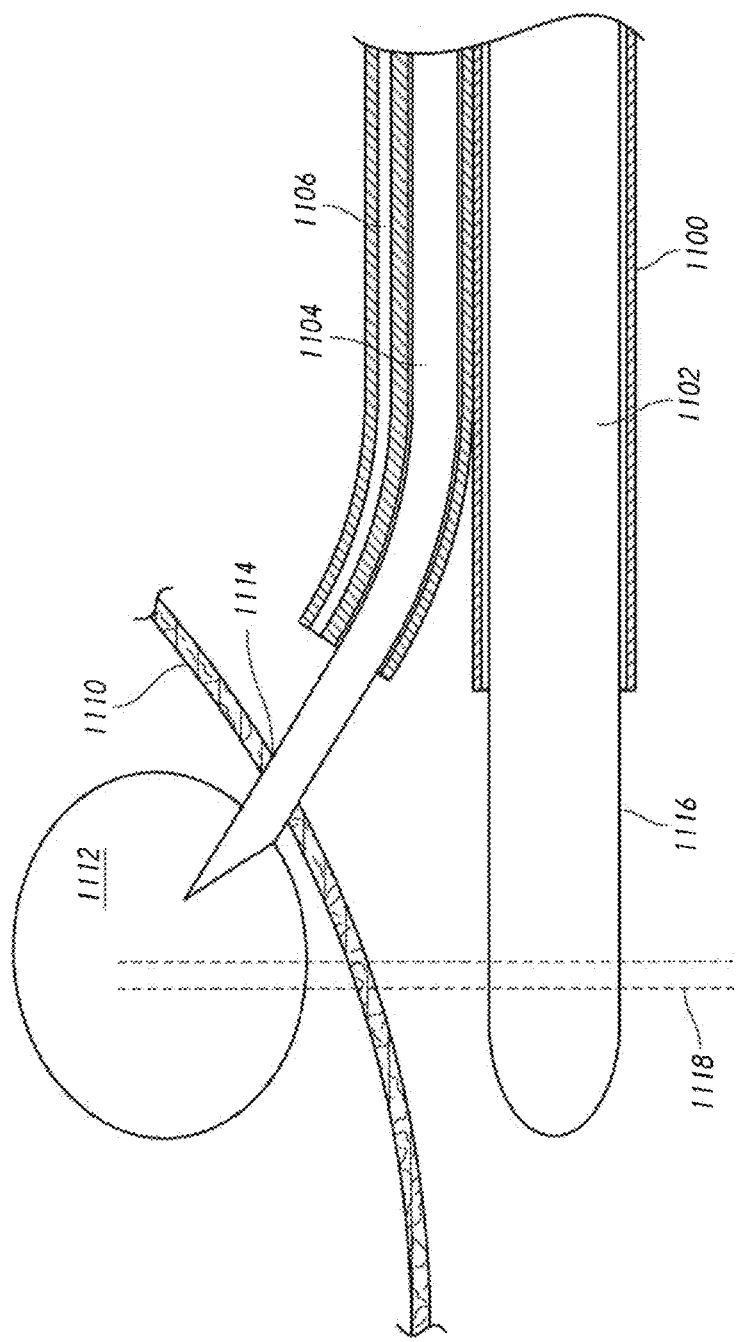

DEVICE FOR VISUALIZING REAL-TIME SAMPLING

CROSS REFERENCE TO RELATED APPLICATIONS

This application is a Continuation of U.S. patent application Ser. No. 14/199,245 filed on Mar. 6, 2014, which claims priority to and the benefit of U.S. provisional patent application Ser. No. 61/779,483 filed on Mar. 13, 2013 entitled "Device for Minimally Invasive Delivery of Treatment Substance," the entire disclosures of which are hereby incorporated by reference.

BACKGROUND

Description of the Related Art

Early diagnosis of potentially cancerous tissue is an important step in the treatment of cancer because, the sooner that cancerous tissue can be treated, and the better the patient's chances are for survival. Typical diagnostic procedures involve biopsying tissue at a site of interest. In the case of lungs, lung cancer can be difficult to diagnose due to the difficulties in accessing airways near areas of interest. Areas of interest may present as lung nodules—small tissue masses in the lung that may range in size between 0.5-30 mm—that typically are biopsied to ascertain whether the tissue therein is cancerous or otherwise diseased. In some instances treatment of tissue in an area of interest can include delivery of chemicals (e.g., ablative chemicals) or other substances.

Existing systems typically are constrained by difficulties in accessing lung nodules, especially in the smaller peripheral airways that may be too narrow to accommodate larger catheters and biopsy/substance delivery apparatuses. Further, the biopsy/substance delivery needles normally are straight and relatively inflexible. Thus, the biopsy/substance delivery needles can limit the articulation of a bronchoscope or can be difficult to pass through a working channel of a bronchoscope when the bronchoscope is articulated around a tight corner. In some instances, the material of the needle may inelastically yield, which can result in a bent needle that is difficult to control. In addition, the straight biopsy needles obtain samples along an axis of the needle through back and forth cycling of the needle. Thus, obtaining multiple samples from different regions of a single nodule, for example, can be difficult and can require repeated repositioning of the bronchoscope or guide sheath, for example. Furthermore, delivery of substances to different regions of a single nodule can be difficult.

SUMMARY

Accordingly, embodiments described herein relate generally to methods, systems, and devices for navigating to and biopsying tissue at a site of interest. In particular, embodiments described herein may be used for biopsying tissue in a lung (such as lung nodules or lymph nodes) using a flexible transbronchial biopsy aspiration needle system. Certain embodiments provide for the flexible biopsy needle to be steerable or guidable to a location of interest. Further embodiments provide for a visualization system (e.g., ultrasound) to be provided in a flexible, miniaturized configuration, and this visualization system may be combined with the flexible biopsy needle.

In one aspect of the present invention, a system includes a bronchoscope having an insertion tube having a working channel. Also, the system includes a catheter received within the working channel. The catheter includes a first lumen extending from a proximal end of the catheter to a distal end of the catheter and a second lumen extending from the proximal end of the catheter to the distal end of the catheter. An ultrasound probe is slidably received within the first lumen and a tissue sampling device is slidably received within the second lumen.

In another aspect of the invention, the catheter includes a mechanism for adjusting the angle of the distal tip of at least one of the first lumen, the second lumen or the tissue sampling device. The mechanism includes one or more steering wires. The steering wires may include a Bowden wire.

In still another aspect of the invention, the ultrasound probe is a radial ultrasound probe that generates at least one real-time ultrasound image of at least one of the tissue sampling device or surrounding tissue.

In yet another aspect of the invention, the tissue sampling device includes a lumen extending from the proximal end of the catheter to the distal end of the tissue sampling device. The system includes a guidewire received within the lumen of the tissue sampling device.

In further aspects of the invention, the guidewire includes a shape memory material with a portion being set in a curved configuration. The tissue sampling device includes a flexible section. When the portion of the guidewire is received within the flexible section, the flexible section of the tissue sampling device bends away from a longitudinal axis of the catheter.

BRIEF DESCRIPTION OF THE DRAWINGS

The foregoing and other features, aspects and advantages of the present disclosure are described in detail below with reference to the drawings of various embodiments, which are intended to illustrate and not to limit the disclosure. The drawings comprise the following figures in which:

FIGS. 3A-G illustrate various configurations for interruptions that may be made along one or more portions of embodiments of the flexible needles.

FIG. 4 illustrates a close-up view of the flexible shaft portion of an embodiment of a flexible needle.

FIGS. 11A-B illustrate front and side cross sectional views of an embodiment of a multi-lumen, steerable catheter in a relaxed state. FIG. 11C illustrates a side cross sectional view of the catheter in an articulated state.

DETAILED DESCRIPTION

Various embodiments of a flexible transbronchial needle aspiration system, a minimally invasive substance delivery system, and their related components and parts will now be described with reference to the accompanying figures. The terminology used in the description presented herein is not intended to be interpreted in any limited or restricted manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the disclosure herein described. For example, while references may be made herein to using the embodiments described herein with terms such as "lung," "airway," "nodule," and so forth, these terms are broad and the embodiments described may be used without limitation and unless otherwise indicated can be used to access to other vessels, passages, lumens, body cavities, tissues, and organs present in humans and animals. For example, lumens such as the gastrointestinal system may be accessed with the embodiments described herein.

Figure 1:
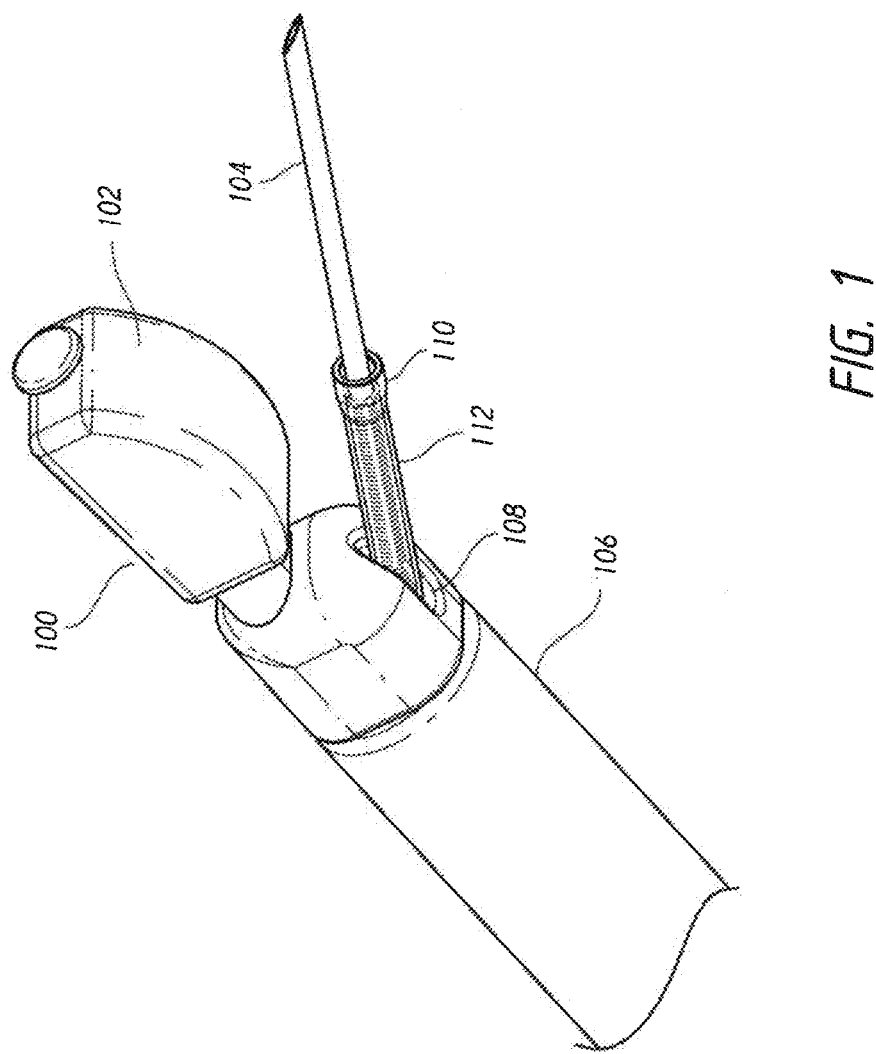
FIG. 1 is a perspective view of a transbronchial needle aspiration system comprising an ultrasound sensor.

Presently, various companies offer products directed to transbronchial needle aspiration systems, some of which include visualization systems to direct the needle to a site to be biopsied. For example, Olympus manufactures an ultrasound system (the Endobronchial Ultrasound Transbronchial Needle Aspiration system (EBUS-TBNA)) substantially as illustrated in FIG. 1. As shown, the system 100 employs an ultrasound probe 102 situated at the distal end of a specialized bronchoscope 106. A rigid needle 104 extends at an angle from an aperture 108. The needle 104 is sheathed prior to deployment by a catheter or sheath 110 that contains coils 112. The coils 112 preferably surround the needle 104 to reduce the likelihood of the needle 104 perforating a working channel of the bronchoscope 106. Because the needle 104 is rigid and its range of motion constrained, the system 100 is limited in the area of tissue that can be easily biopsied. Although some medical practitioners may occasionally bend needles similar to the needle 104 so as to be able to biopsy tissue at larger angles relative to the axis of the bronchoscope, these needles remain rigid (albeit bent) and still limit the area of tissue that can be biopsied.

Figure 2:
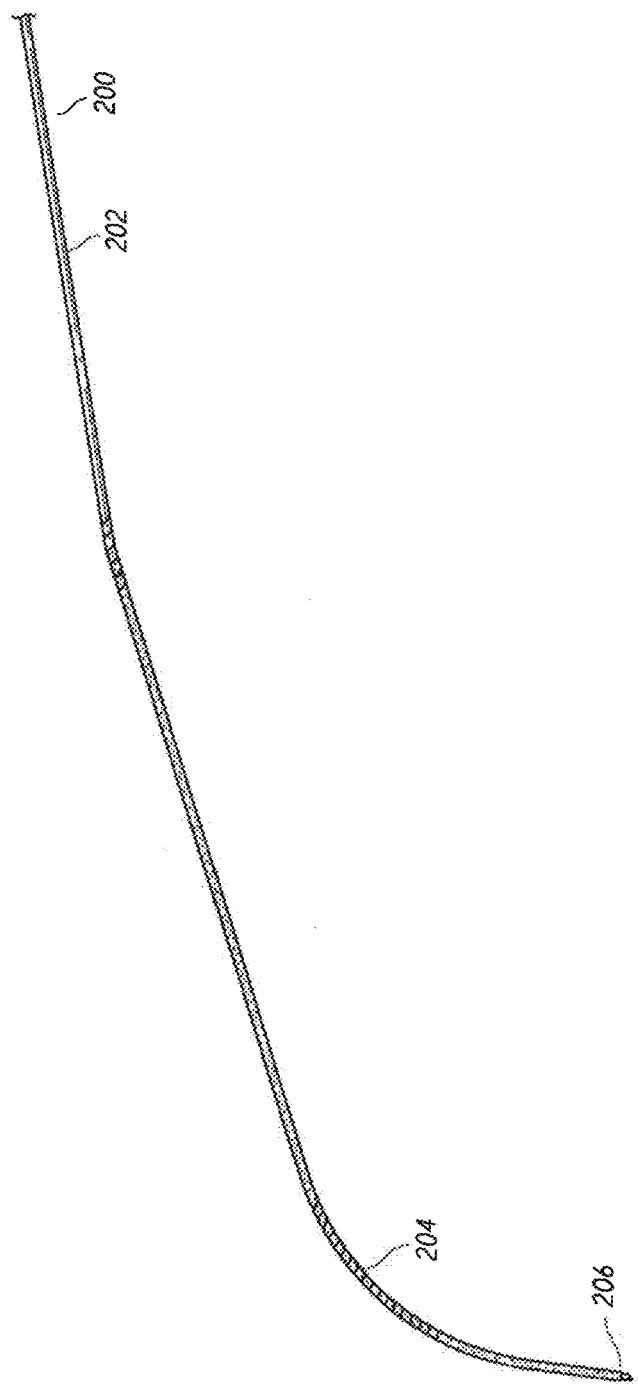
FIG. 2 illustrates a side view of an embodiment of a flexible needle.

FIG. 2 illustrates an embodiment of a flexible needle 200. As will be discussed, embodiments of this flexible needle 200, as well as the other embodiments described herein, may be used in conjunction with existing systems and methods (such as the system 100 illustrated in FIG. 1) for locating, navigating to, and biopsying regions (e.g., lung nodules, lymph nodes) of interest. Use of a flexible needle can permit biopsying tissue and cells in a much larger area and over a wider range of angles compared to existing systems, and certain embodiments allow for greater articulation of a bronchoscope or endoscope so as to gain access to tortuous areas of the anatomy. Accordingly, the use of such embodiments can provide increased sample quality, greater diagnostic yields, and a reduction of erroneous diagnostic results (e.g., false positives or negatives). It will be noted that although bronchoscopes are referred to herein, other endoscopes may be usable (e.g., gastric endoscopes, colonoscopes). As such, other lumens may be explored, navigated to, and biopsied using the embodiments described herein.

A proximal end of the needle 200 includes a proximal shaft portion 202. The distal end includes a flexible shaft portion 204 that is more flexible than the proximal shaft portion and preferably able to selectively bend, curve, and articulate such that the respective ends of the needle 200 are not necessarily collinear. Flexible shaft portion 204 may be provided with a laser cut feature, for example a spiral cut, to improve the flexibility in this region. For example, due to the flexible nature of the needle 200, the needle 200 is capable of at least two different deflections in radial directions to angles that would exceed the yield strength of a solid needle formed of the same material. At the extreme distal end, the flexible shaft portion 204 includes a short distal tip portion 206. This distal tip portion 206 is configured with a piercing tip used to obtain biopsy cell and/or tissue samples. The distal tip portion 206 preferably is more rigid than the flexible shaft portion 204. It is contemplated that the needle is formed unitarily of a single material.

In some embodiments, the flexible transbronchial needle 200 can be advanced to peripheral airways and can easily penetrate into the lung parenchyma. In a preferred configuration, the needle 200 can penetrate tissue at a depth of at least 15 mm. In some embodiments, the distal end 204, 206 of the needle 200 can articulate such that it can bend over 90 degrees relative to a more proximal portion. In a preferred embodiment and when inserted into a bronchoscope working channel (such as the BF-P180™ bronchoscope manufactured by Olympus), the needle 200 can articulate at least 130 degrees when the needle tip 206 is flush with the end of the bronchoscope. When inserted into a system 100 similar to that illustrated in FIG. 1, embodiments of the needle 200 can articulate approximately 110 degrees. Due to its relatively low-profile construction, embodiments of the flexible needle 200 may be miniaturized, in conjunction with a catheter or guide sheath, so as to fit into working channels (e.g., of a bronchoscope) that are as small as or smaller than 2.0 mm. For example, certain embodiments of the needle 200 can be used with small guide sheaths with a minimum inner diameter of 1.7 mm.

The flexible needle 200 can be formed from any suitable material. In some configurations, the flexible needle 200 may be formed from a metal or metal alloy, such as stainless steel, nitinol or the like. In some arrangements, the flexible needle 200 can comprise a polymer or other suitable covering over at least a portion of the length of the flexible needle 200. In some configurations, the flexible needle 200 can comprise a heat shrink material that covers substantially the entire length of the flexible needle 200. In some configurations, one or more of the inner and outer surfaces can receive a coating of any suitable material. The coating can improve the lubricity of the coated surface or increase the smoothness of the coated surface. In some configurations, the flexible needle 200 is constructed from a hypotube. Preferably, the hypotube is constructed to be relatively smooth along at least a proximal portion such that when introduced into a device such as a catheter lumen, for example but without limitation, the hypotube is able to relatively freely slide, rotate, or otherwise move along the lumen.

Embodiments described herein (for example but without limitation, the embodiment illustrated in FIG. 2) may be used with any suitable visualization device, such as the ultrasound system 100 of FIG. 1, navigation system or the like. By using the flexible transbronchial needle 200, access to regions of interest in the lung or in other tissues can be easier and more straightforward, because the flexible needle 200 is able to articulate, bend, and/or curve to a greater degree than a straight, inflexible needle, and independently from the angle or articulation that a bronchoscope or endoscope may have at the same time. This may, for example, enable biopsying of tissue at an angle close to perpendicular from the bronchoscope. In addition, the flexible needle 200 can bend in a region between the distal piecing tip 206 and the distal end of any protective guide sheath or catheter. Further, the coils 112 present in the sheath 110 of the existing system 100 can be made shorter or eliminated entirely due to the flexibility of the needle. In other words, the flexibility of the distal portion 204 of the flexible needle 200 reduces the likelihood of perforating the working channel of the bronchoscope. The increased flexibility also decreases the radial forces exerted by the distal tip 206 of the needle 200 during navigation through the working channel of the bronchoscope, for example but without limitation.

In some embodiments, visualization of the needle 200 may be enhanced (in particular for ultrasound) by including signature markers 2059 that will enhance the visibility of the needle 200, particularly at the distal tip. Signature markers may include forming dimples, scallops, a spiral scribe which may be laser cut, or the like on the needle 200, which dimples, scallops, a spiral scribe which may be laser cut, or the like can reflect ultrasound. Such features provide echogenic surface for detection by ultrasound. Of course, other markers visible for different visualization methods can be used, such as radiopaque markers located on various elements of the catheter or sheath used to deploy the needle 200, as well as the needle 200 itself.

Although ultrasound has been found to be a preferable system for visualization due to the relatively high penetration depth (10-18 mm) of ultrasound, other systems also may be used. In some configurations, a spiral ultrasound probe can be used to provide improved visualization over an ultrasound probe that provides visualization in only a single plane. Other systems for locating and navigating to tissues of interest, such as lung nodules and lymph nodes, may include using a bronchoscope with an optical channel, fluoroscopy, optical coherence tomography, and magnetic resonance imaging. Any other suitable navigation systems also can be used, including commercial systems using X-ray computed tomography assisted visualization (such as, for example but without limitation, the Bf Navi™ system sold by Olympus and the i-Logic™ system sold by SuperDimension).

FIGS. 3A-G illustrate various configurations for flexibility increasing features (e.g., slots, openings, or grooves) that may be formed along various regions of transbronchial needles to increase flexibility. For example, such flexibility increasing features may be made into the flexible shaft portion 204 of FIG. 2. Generally, one or more flexibility increasing features, or cut patterns, 304 such as cuts for example but without limitation, may be made onto the needle wall 300 of the needle; these cuts 304 may then define one or more regions of increased flexibility 302. These cuts 304 permit the region of increased flexibility 302 on the flexible shaft portion to selectively articulate and bend more easily and to a greater degree than an equivalent portion that is uncut, thereby permitting navigation and biopsying of tissue in tortuous regions of, for example, an airway that may not be possible using a traditional rigid needle.

The flexibility of the region of increased flexibility 302 may be tailored as desired for a particular application. The flexibility can be changed, for example, by modifying the thickness of the needle wall 300, the materials used therein, and the spacing, pitch, and angle between the flexibility increasing features 304 in the region of increased flexibility 302. Preferably, the cuts 304 extend in a spiral fashion along the region of increased flexibility 302. In preferred embodiments, the features 304 are cut with a thickness between about 0.0010 and about 0.0025 inches, and even more preferably a range between about 0.0015 and about 0.0020 inches.

Figure 3A:
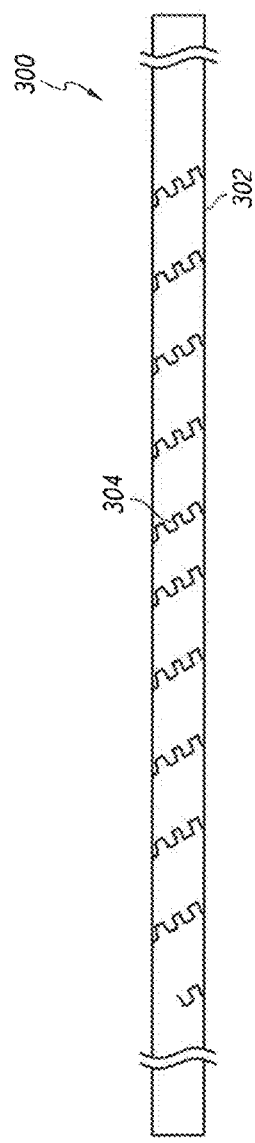
Figure 3B:
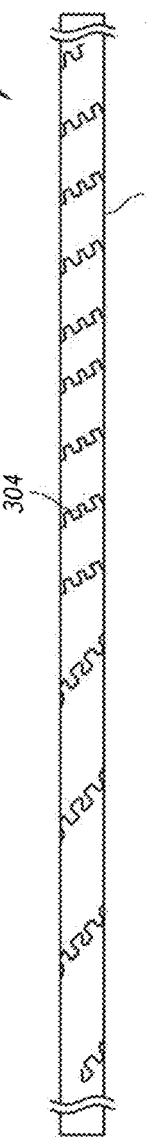

Additionally, the region of increased flexibility 302 does not need to have features such as the single pitch illustrated in FIG. 3A, but, with reference to FIG. 3B, can instead have features that are of a variable pitch, wherein the spacing or pitch can be changed in a continuous or stepwise fashion, for example but without limitation. Additionally, although the cuts shown in these figures are made in a continuous and single cut, high flexibility regions may be made using one or more discontinuous cuts. In these figures, the flexibility increasing features 304 that constitute the region of increased flexibility 302 are made in a "jigsaw" configuration that forms a sawtooth or zigzag pattern. Other possible features can have a pattern that is a "serpentine" configuration where the cuts are smoother, more rounded, and with a longer amplitude than the jigsaw pattern, for example but without limitation. Other types are possible and envisioned, including straight cuts, partial or dashed cuts, zigzag cuts, sinusoidal cuts, and so on. In some configurations, axially asymmetric cuts may be made so as to enhance flexibility in only one direction relative to the axis, for example as discussed below in relation to FIG. 3F. Moreover, continuous patterns are desired over interrupted patterns because of improved resistance to fatigue failures and improved flexure characteristics.

Figure 3C:

FIG. 3C illustrates an embodiment of the region of increased flexibility 302 comprising overlapping discontinuous straight reliefs 304, each extending around approximately half of the circumference of the needle wall 300 in the illustrated configuration. In this embodiment, holes 306 may be provided at one or more of the ends of each relief. The holes 306 may in some cases be made as part of a laser cutting process used to create the reliefs 304, although the reliefs 304 and/or the holes 306 may be made using any suitable process, for example chemical etching or water jetting. The holes 306 may also be useful in providing additional strength to the needle wall 300, as it is believed that the holes 306 may aid in reducing or eliminating the likelihood of crack propagation when the needle wall 300 undergoes various stresses.

Figure 3D:
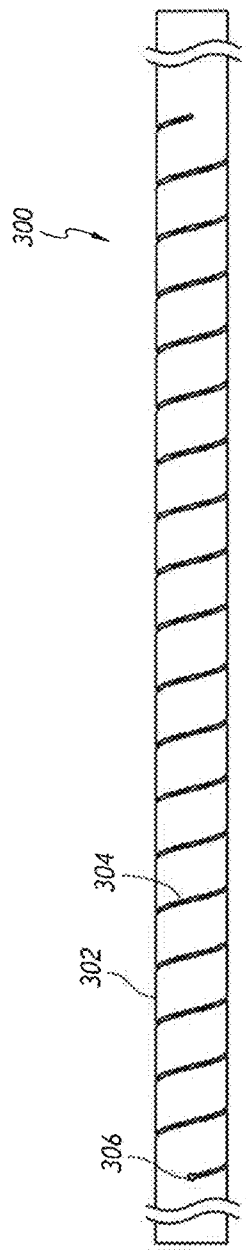

FIG. 3D illustrates an embodiment with a region of increased flexibility 302 comprising a single, continuous spiral cut 304. Holes 306, similar to those described above, may be present at the respective ends of the cut 304. Preferably, and as illustrated here, the pitch is substantially constant throughout the length of the cut 304; in some embodiments, however, one or more portions of the cut 304 may have a varied pitch. In some embodiments, a region of increased flexibility 302 may be manufactured that resembles the embodiment illustrated here by using a closely-spaced stacked wire, flat wire coil or cable tube. Of course, other embodiments may be manufactured using other types of cutting (e.g., laser cutting) discussed herein.

Figure 3E:
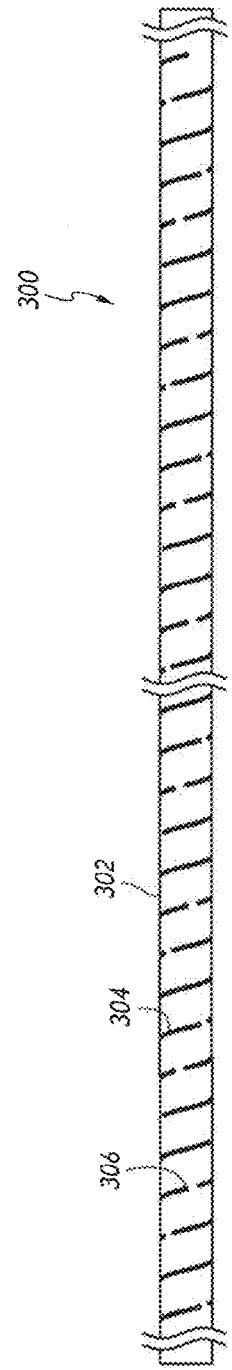

FIG. 3E is similar to the embodiment illustrated in FIG. 3C. Here, however, the region of increased flexibility 302 includes an interrupted spiral pattern where the tube has cut and uncut portions along the same spiral path 304 that have substantially the same pitch along the entire length of the region 302.

FIG. 3F illustrates an embodiment with an asymmetric region of increased flexibility 302. Here, cuts 304 can be positioned along only one side of the needle wall 300; in other words, the cuts 304 are arranged such that only a portion of the entire radial circumference along the axial length of the needle wall 300 is interrupted. In other words, when viewed along a certain direction along the axial length of the needle wall 300, the cuts 304 forming a region of increased flexibility 302 will be seen along at least a portion of one of the sides, while a side opposite the cuts 304 will be substantially lacking cuts. Arranged in this manner, the flexibility of the needle wall 300 along the region of increased flexibility 302 will be asymmetrically flexible so as to permit increased bending or flexibility in one direction or plane while being less flexible in another direction.

Embodiments of needle walls 300 with asymmetrical regions of increased flexibility may be useful in conjunction with bronchoscopes or other navigational devices by increasing the maneuverability of the needle wall 300 while in the bronchoscope. In particular, some bronchoscopes may be more adapted to bending in a particular plane—alignment of the asymmetrical region of increased flexibility 302 in this plane may thus be useful. For example, asymmetric bending of the needle wall 300 can force the needle wall 300 to rotate about its longitudinal axis as the navigational device bends and flexes. Such rotation can help to ensure that certain features of the needle could be maintained in a substantially consistent alignment with regard to the navigational device. For example, the bevel of the distal tip of the needle and/or ultrasonic reflective zones of the needle walls 300 could be maintained at a substantially consistent rotational orientation with respect the navigational device (e.g., a bronchoscope). Further, rotation of the needle wall 300 along its axial length may also aid navigation and maneuverability, as certain embodiments with asymmetrical regions of increased flexibility 302 have been demonstrated to rotate in the path of least resistance, typically the smallest possible radius.

The cuts 304 may not necessarily be straight and perpendicular to the longitudinal axis of the needle wall 300. As illustrated in FIG. 3G, the cuts 304 that comprise the asymmetrical region of increased flexibility 302 may be contoured, and may preferably further comprise a hole 306 located in at least one of the ends 310 of one or more of the cuts 304.

Several characteristics of the cuts 304 may be altered to tailor the stiffness, bending resistance, torqueability, and other material parameters of the region of increased flexibility 302. For example, the kerf, or cut width, in each cut 304 may be larger at some points than at others, which may enhance flexibility. In some embodiments, the kerf at a midpoint 311 of a cut 304 may be wider than the kerf at one or more of the ends 310. In such a configuration, the flexibility may be increased when the needle wall 300 is bent in the direction or plane of the asymmetrical region of increased flexibility 302, while reducing or minimizing flexibility (progressively or in a stepwise manner) as the bend location moves away from the direction or plane of the region of increased flexibility, as a result of the change in kerf toward the ends 310. It may also be preferable to have a thinner kerf to reduce the amount of torque that can be applied to the needle wall 300 before the tube interlocks. Additionally, the kerf may be modified along the length of the region of increased flexibility 302. For example, the kerf in a proximal section may be wider and taper to a narrower kerf at the distal end, which may provide for a needle wall 300 that is flexible but that will stiffen when rotated.

Other characteristics of the region of increased flexibility 302 may be modified. In addition to the kerf, the pitch spacing, the length and/or amount that a cut 304 extends around the needle wall 300, and the distance between cuts 304 may be modified to tailor the wall 300 as desired. In some embodiments, the minimum longitudinal distance point between the cuts 304 can be varied along the length of the needle wall 302. In some such embodiments, the flexibility of the needle wall 302 can vary along the length of the needle (e.g., more flexibility as the minimal longitudinal distance between the cuts 304 is reduced). Accordingly, the flexibility, torqueability, and other characteristics of the region of increased flexibility may be modified. Further, some embodiments may provide for a needle wall 300 comprising multiple asymmetrical regions of increased flexibility 302. In some embodiments, the multiple regions 302 may be staggered at differing orientations, for example in mutually orthogonal directions (i.e., at 90° angles to each other).

In practice, in tailoring the region of increased flexibility 302 and the reliefs 304 that can constitute this region of increased flexibility 302, it may be desirable to find a suitable balance between the flexibility required and the type of relief. For example, while wider or larger reliefs may provide additional flexibility, these may in some cases weaken the needle wall 300 to an unacceptable extent. Different patterns also may perform more or less satisfactorily in fatigue testing. Additionally, certain patterns may cause portions of the region of increased flexibility 302 to abrade the working channel of the catheter or other instrument the needle is inserted in, or else the tissue being biopsied (although this may be desirable in certain applications, as described below). Post processing after creation of the reliefs may include steps such as deburring, electropolishing, extrude honing, microblasting, or ultrasonic cleaning, which may at least partially alleviate or reduce such concerns. The type of reliefs 304 described above may also be adjusted in accordance with the length of the one or more regions of increased flexibility 302. Prototypes have been constructed with regions of increased flexibility measuring approximately 3-4 cm. Preferably, the extreme distal end of the needle wall 300 is left uncut or otherwise generally solid to reduce the likelihood of buckling and so that a piercing point can be made onto the needle. In some arrangements, the piercing point is ground or honed and the generally solid portion of the extreme distal end assists in the formation of a point or tip. In some embodiments, the generally solid distal region measures between about 8 mm and about 10 mm. Other configurations are possible.

FIG. 4 shows an embodiment of a flexible transbronchial needle 400 that includes a distal tip portion 402 and a flexible region 404. In one embodiment, the distal tip portion 402 has a sharply angled tip to core or scrape cells from tissue to be sampled. The flexible region 404 preferably includes one or more reliefs or cuts 406. In one embodiment, the cuts 406 are a jigsaw cut. In other embodiments, the cuts 406 may be a different type of cut, for example as described above in FIGS. 3A-G. In one embodiment, a covering 408, which may comprise polymer coatings and/or heat shrink wrap, can be used to cover the cuts 406 on the needle 400. The covering 408 may in some embodiments also comprise coils of a resilient material (e.g., metals or polymers) that surround at least a portion of the flexible region 404 to provide additional support against buckling or collapse, while remaining flexible enough to provide selective articulation and/or bending of the needle 400.

Obtaining a cored tissue sample may be preferable for pathology or histology samples where a largely-intact sample of tissue is desired. For such applications, the needle is preferably in a relatively larger size range of approximately 17-19 gauge, possibly with a smaller 21 gauge needle within. Such needle sizes have been found to produce a "cored" tissue sample satisfactory for histology applications. Obtaining biopsy cells and fluid for cytology may however use a smaller, non- or minimally-coring distal tip portion 402, for example. Because biopsies for cytological applications typically apply suction while performing agitation (moving back and forth) of the needle in the biopsy site, sharper and/or rougher needles may perform better and obtain additional cells. For such applications, smaller needle sizes in the range of 21-23 gauge may also be preferable. In some embodiments, the distal tip portion 402 may be cut and/or angled differently for different applications. In some applications, a hole, port, slot or other structure also can be provided just proximal of the distal end. In some applications, the hole, port, slot or other structure can be provided on a surface of the needle that is opposite from the surface of the needle having the most proximal portion of the beveled opening formed at the tip. In some applications, the hole, port, slot or other structure is positioned within a region defined between the distal tip and the most proximal portion of the opening formed by the beveled surface of the opening at the tip. A vacuum source may also be provided so as to aspirate a tissue sample or samples. Other configurations also are possible.

The cuts 406 on the flexible region 404 may be suitable for cytological biopsy procedures. Here, a cut may provide rougher edges that can scrape cells along the path of the needle 400. For example, when the interrupted surface of the needle is bent, the cuts can create a scalloped surface. In particular, sinusoidal, "jigsaw," "serpentine," or zigzag cuts may provide for rougher edges, which—especially when the needle 400 is bent or articulated—can abrade the surrounding tissue and thus sample additional cells. These abraded cells can then be aspirated via the needle 400 along with any other sample being biopsied. If no coating and/or heat shrink wrap 408 is present over the cuts 406, the resulting small openings may also be used to aspirate the abraded cells into the needle 400. Such an uncoated portion of the cut section 406, if present, is preferably located at the distal end of the needle 400 such that surrounding tissue may ingress into the inner lumen during suction.

To increase this scraping or scalloping effect, several steps may be taken. If the cuts 406 are made by water jetting, the needle 400 may be extrude honed to push burrs outward, increasing the roughness of the flexible region 404. Likewise, laser cutting the cuts 406 may in some cases provide additional roughness. In some cases, a polishing or deburring step may be necessary. Dimpling or grinding of the cuts 406 and/or the region 404 may also be useful. The kerf (or width) of the cuts 406 may also be increased, either in part or in whole, along the flexible region 404, which may consequently enhance the scraping or scalloping effect.

The needle 400 may also be flushed after being withdrawn so as to obtain any remaining cells. In some cases, the operator using a needle 400 with cuts 406 will preferably navigate the needle 400 so as to reduce the likelihood of abrading or puncturing blood vessels in the biopsy region, because the resulting jagged edges may take longer to stop bleeding than a cut resulting from a biopsy needle lacking cuts. In some configurations, a dual-needle configuration, with a relatively smooth needle used to puncture into the biopsy site, followed by larger diameter, flexible needle that can include scalloped surfaces that can be used to scrape the tissue. Quick-clotting or cauterizing features could also be incorporated into the needle 400 or various other system components to minimize bleeding when piercing tissue.

Figure 5:
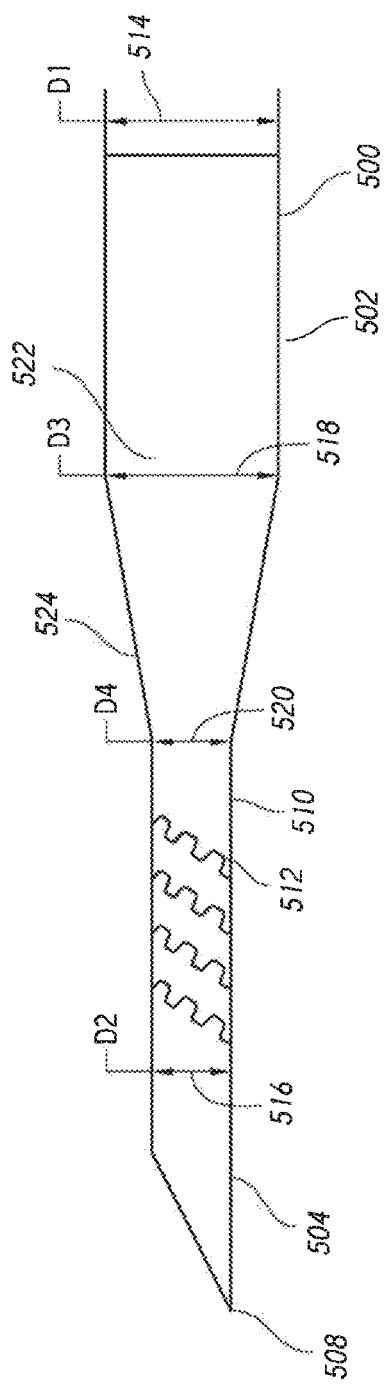
FIG. 5 illustrates a side view of another embodiment of the flexible needle.

FIG. 5 illustrates an embodiment of a flexible transbronchial needle 500. The needle 500 includes several interconnected portions. A proximal end of the needle 500 includes a less flexible shaft portion 502. A distal end of the needle 500 includes a more flexible shaft portion 504. The less flexible shaft portion 502 and the more flexible shaft portion 504 can be connected together by the tapered shaft section 524 in the illustrated configuration. In some configurations, however, the less flexible shaft portion 502 and the more flexible shaft portion 504 can be integrally formed. The more flexible shaft portion 504 includes a distal tip portion 508 and a cut section 510. Cuts 512 are located within the cut section 510. The cuts can be formed in any suitable manner. In one embodiment, the cuts 512 are a "jigsaw" cut, as described above with reference to FIGS. 3A-C. In other embodiments, the cuts 512 may be cut differently.

This embodiment of a flexible transbronchial needle 500 has several advantages, as on one hand the needle 500 becomes more torquable and pushable while also retaining flexibility at its distal end. The less flexible shaft portion 502 at the proximal end is preferably more rigid and stiffer than the more flexible shaft portion 504, so as to facilitate torque and force transmission to the thinner, more flexible shaft portion 504. In one embodiment, this is accomplished by constructing the needle 500 so as to become progressively thinner from the proximal end to the distal end, such that the flexible shaft portion 504 remains flexible and bendable. By constructing the needle 500 in a manner that it becomes thinner at the tapered shaft portion 524, the needle becomes more flexible, while also reducing resistance to rotation in the distal end comprising the flexible shaft portion 504. Additionally, the more rigid portion 502 is more durable and better able to transmit torque or force, while being situated in a portion of the needle 500 where flexibility is less important.

The less flexible shaft portion 502 has an outside diameter D1 514. The more flexible shaft portion 504 has an outside diameter D2 516. The tapered shaft section 524 has a proximal end 518 and a distal end 520, with the outside diameter D3 522 being located at the proximal end of the tapered shaft section 518 and the outside diameter D4 520 being located at the distal end of the tapered shaft section 520. Preferably, the outside diameter D3 522 is equal to the outside diameter D1 514. The outside diameter D4 520 is preferably equal to the outside diameter D2 516. The outside diameter of the tapered section 524 may vary linearly or nonlinearly between D3 and D4. It will also be understood that in some embodiments, the tapered section 524 may extend into all or part of the flexible shaft portion 504 and/or the less flexible shaft portion 502, and that in some embodiments there may be additional tapered sections. Further, although the tapered section 524 reduces in diameter going in a proximal to distal direction, the opposite configuration may be useful in some embodiments.

Typically, the portions 502, 524, 504 will be constructed from a length of material (e.g., metals such as stainless steel or nitinol) of a substantially uniform thickness, and as such, the inside diameters of the respective portions will generally correlate to the outside diameters referred to above. However, it is contemplated that materials of varying thicknesses may be used to construct the needle, and the thickness defined by the inside and outside diameters may differ along the length of the device. This may be accomplished, for example, by constructing the needle 500 in a piecewise fashion from separate parts, or by drawing out the needle in a single unit so as to create sections of varying thickness. Such varying thicknesses may be used, for example, to tailor factors such as the rigidity, strength, torquability, or flexibility of the resulting needle to the desired application.

FIGS. 6A-D illustrate different embodiments of steerable, flexible transbronchial needle aspiration assemblies. Such assemblies may be manipulated by an operator to steer the needle to a site identified to be of interest. Preferably, such assemblies may also permit a flexible needle to be steered independently of a bronchoscope or other endoscope. While the examples discussed below in FIGS. 6A-D discuss a needle aspiration assembly, in some embodiments, a guide sheath provided with the steerable features discussed below may also be used. In such an embodiment, a needle, preferably a flexible needle, may be insertable there through.

Figure 6B:
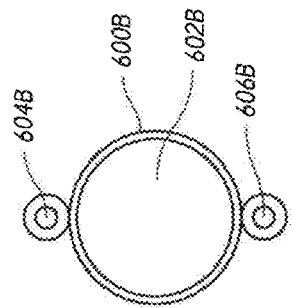
FIGS. 6A-D illustrate schematic cross-section views of different embodiments of a steerable, flexible needle assembly.
Figure 6D:
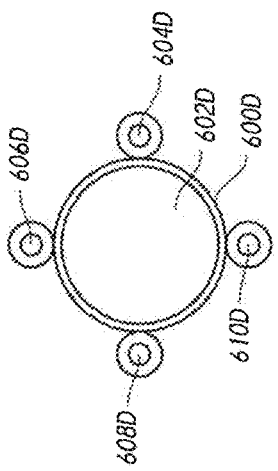
Figure 6A:
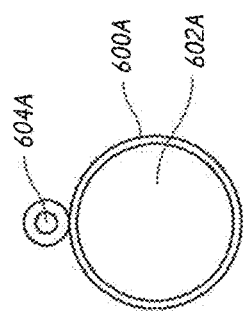
Figure 6C:
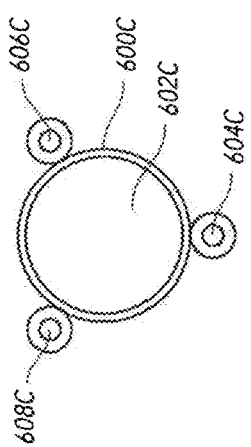

In FIG. 6A, a flexible transbronchial needle aspiration assembly 600A includes a flexible transbronchial needle 602A and a steering wire 604A. In FIG. 6B, a flexible transbronchial needle aspiration assembly 600B includes a flexible transbronchial needle 602B, a first steering wire 604B and a second steering wire 606B. In FIG. 6C, a flexible transbronchial needle aspiration assembly 600C includes a flexible transbronchial needle 602C, a first steering wire 604C, a second steering wire 606C and a third steering wire 608C. In FIG. 6D, a flexible transbronchial needle aspiration assembly 600D includes a flexible transbronchial needle 602D, a first steering wire 604D, a second steering wire 606D, a third steering wire 608D and a fourth steering wire 610D. These steering wires can be arranged in different manners to achieve different steering characteristics. Certain embodiments provide for the steering wires to angle or bend the needle 602 at an angle of up to 45 degrees. Certain embodiments may be small enough to fit within a 2.0 mm working channel of a bronchoscope, and may be miniaturized further.

In these preceding figures, the steering wires may be manipulated by the operator to guide a flexible transbronchial needle to a site of interest. Preferably, this is accomplished by using the one or more steering wires to pull (and thereby bend) the flexible needle in the direction desired. The wires may be attached to the flexible needle in any suitable manner, on the interior or exterior of the flexible needle. In some configurations, the wires are secured by welding them to the flexible needle. When wires are attached to the interior of the flexible needle, such embodiments may allow for insertion into a smaller sheath or working channel. In certain embodiments, this may be accomplished by having the steering wire comprise one or more pull wires. Bowden cables may be used in some embodiments. Nitinol wires, which contract after being heated past a transition temperature may also be used, possibly in conjunction with a heating element controllable by the operator (for example, by using resistive heating).

Figure 7:
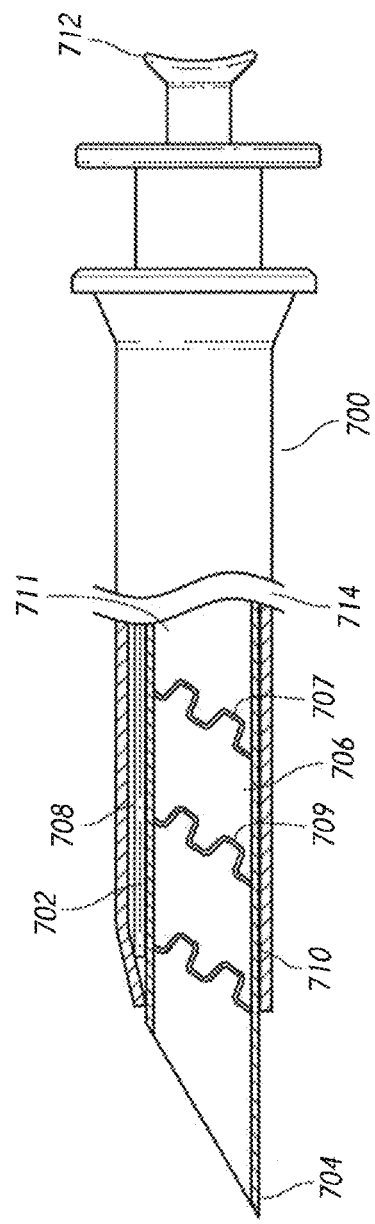
FIG. 7 illustrates a side view of an embodiment of a steerable, flexible needle assembly.

FIG. 7 shows an embodiment of a steerable, flexible transbronchial needle aspiration assembly 700. The needle 700 includes a flexible shaft portion 702 at the distal end. The flexible shaft portion 702 includes a distal tip portion 704 and a flexible section 706 that may be selectively elastically bent or angled such that the respective ends are no longer collinear. The flexible section 706 includes cuts 707 that may be covered and/or sealed with a coating 709, for example a polymer and/or heat shrink. The cuts 707 may be of the type previously described, and could be, for example, "jigsaw" cuts.

In some embodiments, a steering wire 708 is located along the exterior of the flexible shaft portion 702. In other embodiments, multiple steering wires 708 are located along the exterior of the flexible shaft portion 702; these may be arranged as depicted above in FIGS. 6A-D. The steering wire or wires 708 may, as described in FIGS. 6A-D, be used to guide the needle 700 to the site to be biopsied. Preferably, a seal 710 covers at least a portion of the exterior of the steering wires 708 and the flexible shaft portion 702 to reduce the likelihood of the steering wires snagging equipment or body tissue, and preferably is constructed from a pliable polymer.

The proximal end of the needle 700 may be part of or joined to a steel hypotube 711. The proximal end of the hypotube 711 may also have a connection 714 (for example, a luer fitting) so that a source of vacuum (for example, a pump or syringe 712) can be used to pull a vacuum along the length of the hypotube 711. In a preferred embodiment, the hypotube 711 is manufactured from any suitable material.

Figure 8:
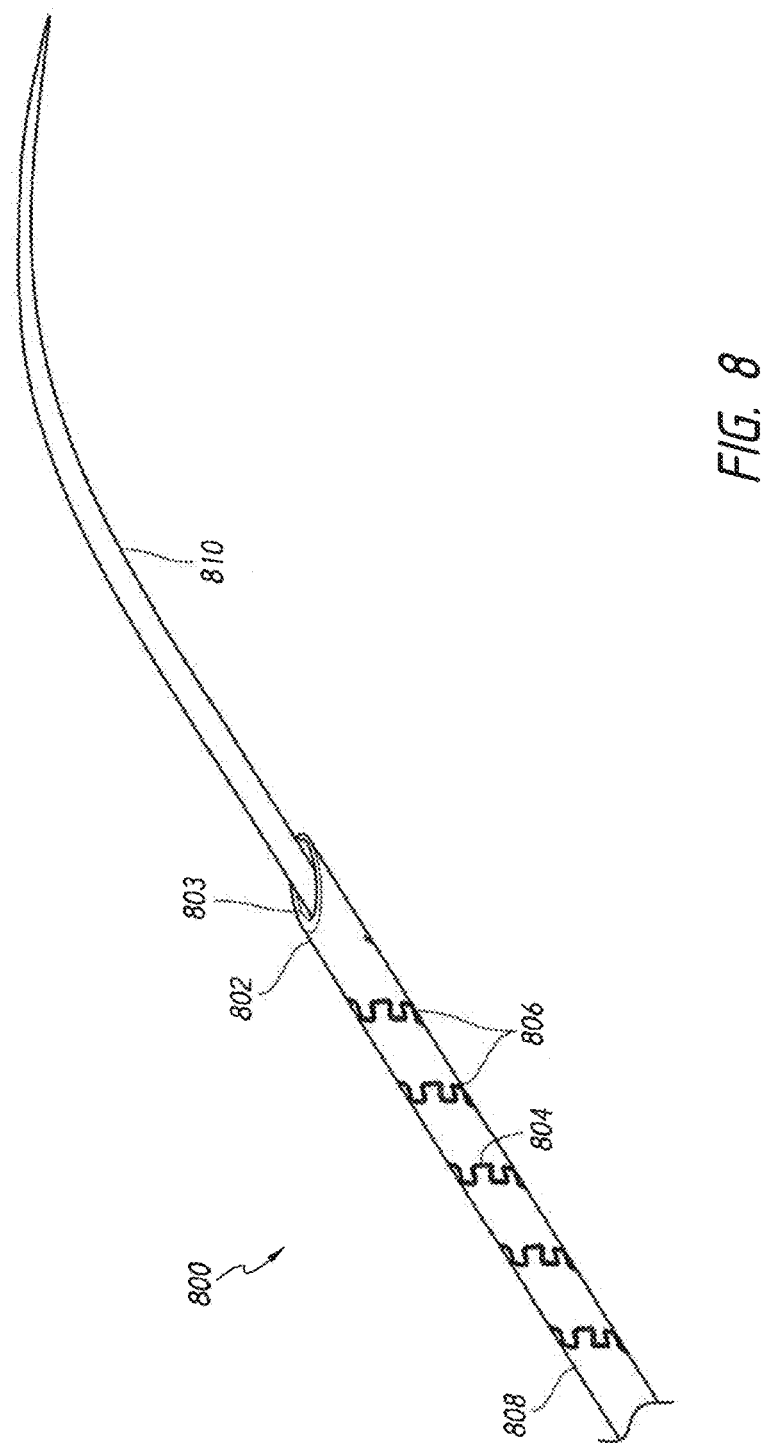
FIG. 8 illustrates an embodiment of a steerable, flexible needle assembly comprising an inner guidewire.

FIG. 8 illustrates an embodiment of a flexible steerable needle 800 comprising an inner guidewire 810. Here, the inner guidewire 810 can be positioned along a central lumen of an embodiment of a flexible needle 800, which may be designed in a similar manner as other embodiments described herein. In some configurations, the guidewire 810 has a length that is greater than the length of the needle 800.

The needle 800 preferably includes a distal tip portion 802 with a distal opening 803. A flexible section 804 preferably is configured to be more flexible than the distal tip portion, and may comprise cuts 806 of the type previously described. These cuts 806 confer additional flexibility to the needle 800 and permit it to bend or curve. In some embodiments, all or part of the flexible section 804 (and the cuts 806) may be covered with a coating 808, which may be a polymer and/or heat shrink, for example but without limitation.

The guidewire 810 preferably is constructed from a shape memory material (metal or polymer) such as Nitinol. Preferably, the guidewire 810 is set in a form that will curve when heated, but is inserted into the needle 800 while in a straightened configuration. While the guidewire 810 is inserted into the needle 800, heating of the guidewire 810 will cause it to curve, thereby curving the needle 800 along its flexible section 804. In some configurations, the guidewire 810 simply is inelastically deformed to provide non-linear region proximate the distal end. In such configurations, simply inserting the guidewire 810 into the needle 800 can cause the needle to bend.

In use, the curved guidewire 810 can be used to steer the needle 810 by rotating the guidewire 810 relative to the needle 810. The curve or bend in the guidewire 810 will cause the flexible portion of the needle 810 to deflect such that the direction of the needle 810 can be varied. In some embodiments, rotational alignment of the curved guide wire 810 with respect to the needle 800 can be controlled using an asymmetric distribution of cuts on the needle wall (e.g., as described above with regard to FIGS. 3F and 3G). For example, asymmetric cuts on the needle wall can cause the needle 800 to rotate about its longitudinal axis as the needle 800 bends to conform to the bent shape of the guidewire 810. In some embodiments, asymmetric cuts in the needle wall help to ensure that the guidewire 810 remains aligned in the same plane of the needle 800 as the bent portion of the guidewire 810 passes through the flexible section 804 of the wire 800. The guidewire 810 may also be used to navigate the needle 800 to the site of interest. Here, the guidewire 810 is guided to the region of interest (e.g., a lung nodule), and the needle 810 is then pushed along the guidewire 810 until the region of interest has been reached. The guidewire 810 may then be withdrawn so as to permit aspiration and biopsying of the region of interest. Partly because the guidewire 810 is located inside the needle 800 and thus provides a very small diameter probe, such a system may be employed to navigate to peripheral lung regions of a reduced diameter and that are inaccessible with a bronchoscope. Additionally, because the guidewire 810 is positioned inside of the needle 800, such a configuration may be preferable for biopsying samples via scraping or scalloping of tissue with the flexible section 804. When the guidewire 810, or another component associated with one or more of the guidewire 810 and the needle 800, is radioopaque, fluoroscopy or the like may be used to navigate the guidewire to a region of interest. Typically, the needle 800 and guidewire 810 are contained within a catheter or sheath. Upon reaching an airway wall proximate to a region of interest, either the needle 800 or the guidewire 810 can be extended into a nodule or other tissue at the region of interest. In some configurations, the needle 800 may extend between 15-20 mm into the adjacent tissue from the end of the catheter or sheath. In some embodiments, the needle 800 may be configured to extend up to about 40 mm into adjacent tissue.

In certain embodiments, the curved guidewire 810 may be part of a system used for providing repeatable access and/or navigation to regions of the lung. Such embodiments are described in Provisional Application Ser. No. 61/604,462, filed Feb. 28, 2012, titled "PULMONARY NODULE ACCESS DEVICES AND METHODS OF USING THE SAME", and the application is hereby incorporated by reference in its entirety. Such embodiments are also described in U.S. patent application Ser. No. 13/778,008, filed Feb. 26, 2013, titled "PULMONARY NODULE ACCESS DEVICES AND METHODS OF USING THE SAME" and published as U.S. Patent Publication No. US 2013-0226026 A1, and the publication is hereby incorporated by reference in its entirety.

Figure 9:
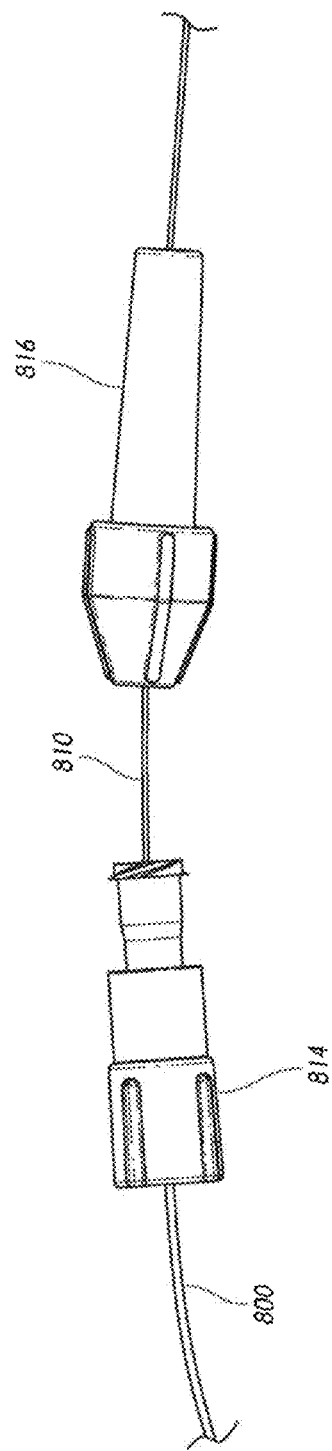
FIG. 9 illustrates the proximal end of an embodiment of a flexible needle assembly comprising an inner guidewire.

FIG. 9 illustrates an embodiment similar to that illustrated in FIG. 8. Here, a connector 814 is connected to the proximal end of the hypotube of the needle 800. The connector 814 used here can be any type of suitable connector, including for example a luer connector. The guidewire 810 is introduced through the connector 814, and at the proximal end of the guidewire 810 is a handle 816 that permits the guidewire 810 to be pushed, pulled, and rotated with respect to the needle 800. After the guidewire 810 has used to guide the needle 800 to the biopsy site, the guidewire 810 is removed from the connector 814. A source of vacuum (e.g., a syringe) is then attached to the connector 814 to aspirate the biopsy sample from the needle 800.

Figure 10:
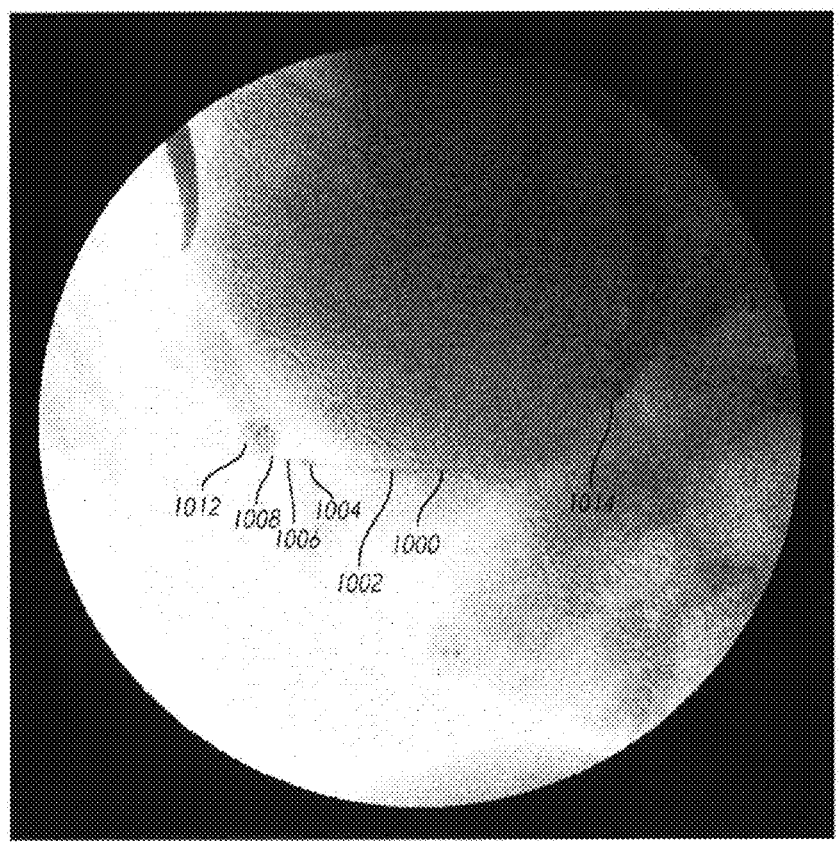
FIG. 10 is a fluoroscopy image of an embodiment of a flexible needle with an inner guidewire.

FIG. 10 is an annotated fluoroscopy image of a curved guidewire similar to that described in FIG. 8 being used to biopsy a lung nodule. Here, the catheter 1000 extends from the distal end of a bronchoscope 1014. The lung passages here were too small to permit navigation of the bronchoscope to an area near the lung nodule, and as such, the catheter 1000 was advanced via fluoroscopy to the suspected nodule site 1012. The distal end of the lumen 1002 containing the flexible needle 1006 also contains coils 1004, which reinforces the lumen 1002 while the needle is located within the lumen and also serves as a fiducial radiopaque marker helpful for visualization of the catheter 1000 in relation to the nodule site 1012. Additional fiducials may also be added to various components of the catheter 1000 (e.g., barium sulfate markers). Extending distally to the needle 1006 is a guidewire 1008, which, being curved, aids in guiding the flexible needle 1006 to the nodule site 1012. In use, the flexible needle 1006 is pushed over the guidewire 1008 to the nodule 1012, the guidewire 1008 is withdrawn and biopsy tissue samples are aspirated through the flexible needle 1006.

A method of obtaining a tissue sample may comprise advancing the bronchoscope 1014 toward a tissue site (e.g., a lung nodule 1012 or lymph node). Within the bronchoscope 1014, the catheter 1000 may be movably disposed. In some embodiments, and preferably when advancing to tissue regions in small or convoluted airways that may not permit navigation with the bronchoscope 1014, a guide sheath surrounding the catheter 1000 may be advanced beyond the bronchoscope 1014 instead of or in conjunction with the guidewire 1008. In some embodiments, the guide sheath may be used without the bronchoscope 1014. The guide sheath may be used in conjunction with a location device, such as fiducial markers (e.g., coils 1004) or an ultrasound probe (e.g., as described below in FIGS. 11A-C). Preferably, the location device is present on the catheter 1000, although a location device may be instead or also present on the guide sheath. Once proximate the tissue site, the catheter 1000 may be advanced beyond the guide sheath and navigated to the tissue site (e.g., using the location device placed thereon) so as to obtain a sample with the flexible needle 1006. The entire assembly may then be withdrawn, or certain portions thereof (e.g., coils 1004) may be implanted proximate the tissue site to serve as a marker.

FIG. 11A shows a cross section view of an embodiment of a multi-lumen, steerable catheter 1100 which may be configured for introduction into a bodily space (for example, pulmonary passages) via an endoscope such as a bronchoscope. The catheter 1100 preferably includes a first lumen 1102 and a second lumen 1104, although other embodiments may comprise a catheter 1100 with more than two lumens. The first lumen 1102 may be larger than the second lumen 1104. In a preferred embodiment, the first lumen 1102 may be used to introduce a miniaturized ultrasound probe, which may then be used to provide real-time location information of the bodily tissues to be examined. For example, when used in the lungs an ultrasound probe can be useful to locate nodules or other locations (e.g., lymph nodes) of suspected or actual cancerous tissue which may be difficult or impossible to locate visually. Preferably, the second lumen 1104 is used to introduce various tools, including but not limited to transbronchial aspiration needles, cytology brushes, biopsy forceps, guiding devices, and so forth.

The catheter 1100 also preferably includes at least one steering wire 1106, which preferably is connected to the second lumen 1104 to permit selective articulation and bending of the distal end of the second lumen 1104. The steering wire 1100 is preferably of the type that may be used in the embodiments described above in FIGS. 11A-D. It is to be noted that whereas the embodiments illustrated in FIG. 8 have an inner guidewire 810 introduced within the inner diameter of the needle 800, the embodiments illustrated in FIGS. 11A-C disclose steering wires positioned on the outside of the needle. This is not to say that the two approaches are mutually incompatible—embodiments may be designed using both inner and outer steering.

FIGS. 11B and C illustrate side views of an embodiment of a multi-lumen, steerable catheter 1100. This catheter 1100 includes a first lumen 1102 and a second lumen 1104. The second lumen 1104 includes a steering wire 1106. FIG. 11B illustrates the second lumen 1104 in a relaxed, non-articulated state.

FIG. 11C shows a side view of an embodiment of a multi-lumen, steerable catheter 1100 used to visualize and conduct a biopsy on a target nodule 1112 located behind an airway wall 1110. Here, the catheter 1100 is illustrated with an ultrasound probe 1116 inserted into the first lumen 1102. The ultrasound probe 1116 is preferably a miniaturized ultrasound probe configured to be inserted into a small catheter or endoscope, and can be for example the UM-S20-175 radial endoscopic ultrasound probe manufactured by Olympus. Such miniaturized ultrasound probes may be advantageous for localization and visualization in peripheral lung passages where visual observation (i.e., via a bronchoscope) is extremely difficult due to the small size of such passages. The second lumen 1104 is illustrated with a flexible needle 1114 inserted therethrough and preferably moveable in a longitudinal back and forth direction so as to biopsy the target nodule 1112. In the illustration, the steering wire 1106 is pulled, thus selectively articulating the second lumen 1104 at an angle with respect to the first lumen 1102. In a preferred embodiment, the needle 1114, when fully extended, can articulate or bend at an angle of about 40 degrees with respect to the first lumen 1102. In some embodiments, the steering wire 1106 may angle or articulate both lumens 1102 and 1104. Some embodiments may also provide for multiple steering wires 1106 capable of both lumens 1102 and 1104 independently. In further embodiments, the steering wires may be provided directly onto the flexible needle 1114 and/or ultrasound probe 1116.

Articulating the distal end of the second lumen 1104 of the catheter 1100 allows tools, in this case distal end of the needle 1114, to be angled toward the target nodule 1112 while the ultrasound probe 1116 remains in the airway providing real-time location confirmation that the needle 1114 has reached the target nodule 1112. Accordingly, the angle of the second lumen 604 preferably is adjusted and aligned such that the needle 1114 and nodule 1112 simultaneously remain in the field of view 1118 of the ultrasound probe 1116. Embodiments of the catheter 1100 have been constructed wherein the needle 1114 is able to articulate up to 20 degrees relative to the ultrasound probe. Some embodiments have been constructed that are compatible with a 3.2 mm bronchoscope working channel, and may be miniaturized further.

Figure 12A:
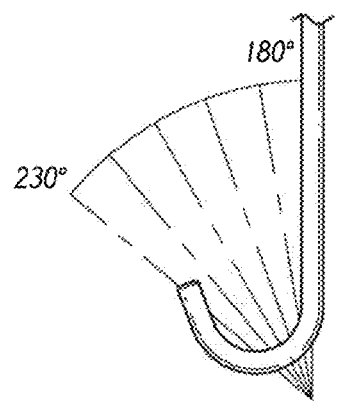
FIGS. 12A-C are illustrations of a bronchoscope showing various degrees of articulation achievable without any biopsy needle, with a conventional straight biopsy needle, and with an embodiment of a flexible biopsy needle.
Figure 12B:
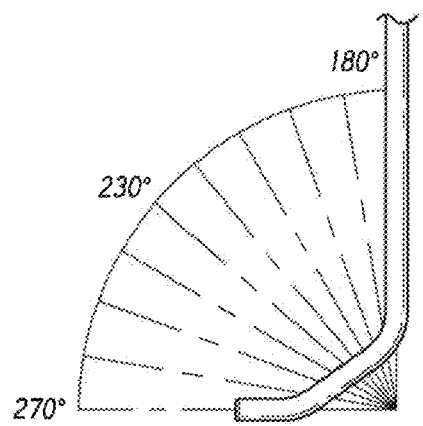
Figure 12C:
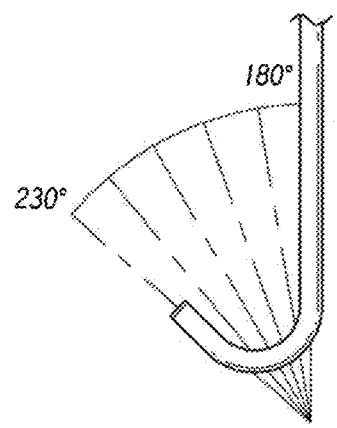

FIGS. 12A-C illustrate a bronchoscope in various degrees of articulation. FIG. 12A illustrates the articulation of a bronchoscope without any biopsy needle inserted within. Here, the angle of articulation is approximately 130 degrees. FIG. 12B illustrates the articulation achievable by the same bronchoscope with a conventional straight rigid biopsy needle and catheter inserted therein. The articulation angle here is only about 90 degrees. Finally, FIG. 12C shows the same bronchoscope with an embodiment of a flexible needle inserted therein. The needle may for example be of the type illustrated in FIG. 2. Due to the flexibility of the needle, the articulation angle achieved here is approximately 130 degrees, and the bronchoscope's overall flexibility is minimally altered in comparison to the bronchoscope without any needle inserted.

Figure 13A:
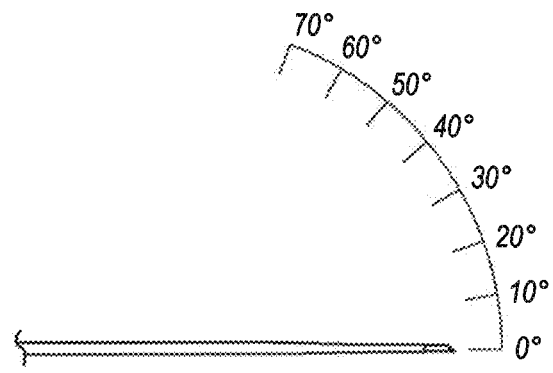
FIGS. 13A-C are illustrations of an embodiment of a flexible needle with steering wires.
Figure 13B:
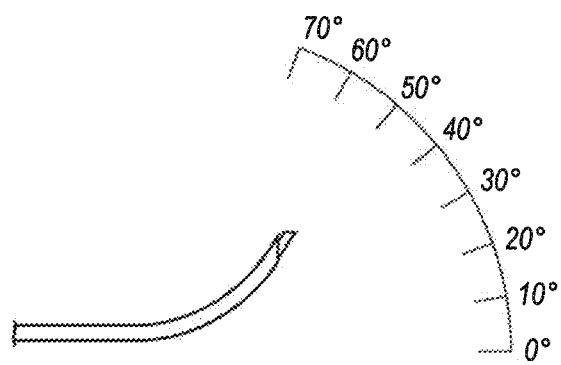
Figure 13C:
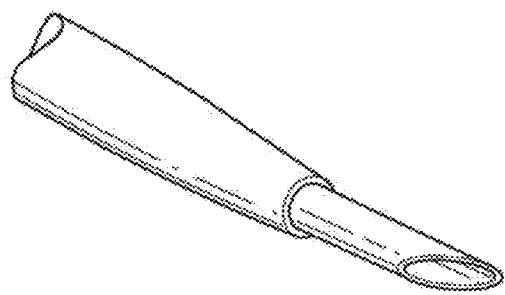

FIGS. 13A-C illustrate an embodiment of a flexible needle with steering wires similar to those illustrated in FIGS. 6A-D and FIG. 7. FIGS. 13A-B show that the needle, with the steering wire pulled, can achieve an articulation of approximately 45 degrees. FIG. 13C illustrates a close-up of the distal end of the needle. A polymeric covering coats or covers the distal end just short of the distal tip of the needle and covers the steering wire or wires underneath.

Figure 14A:
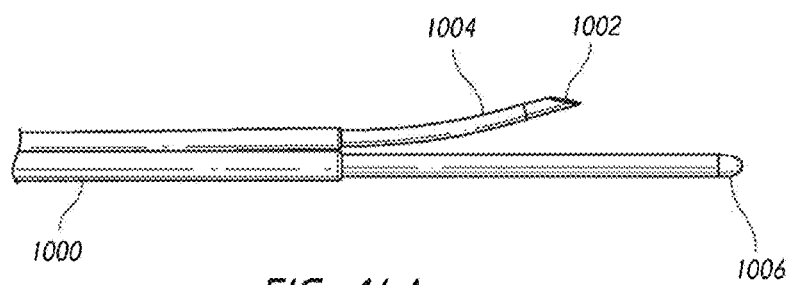
FIGS. 14A-B are illustrations of an embodiment of a flexible needle inserted into a multi-lumen, steerable catheter.
Figure 14B:
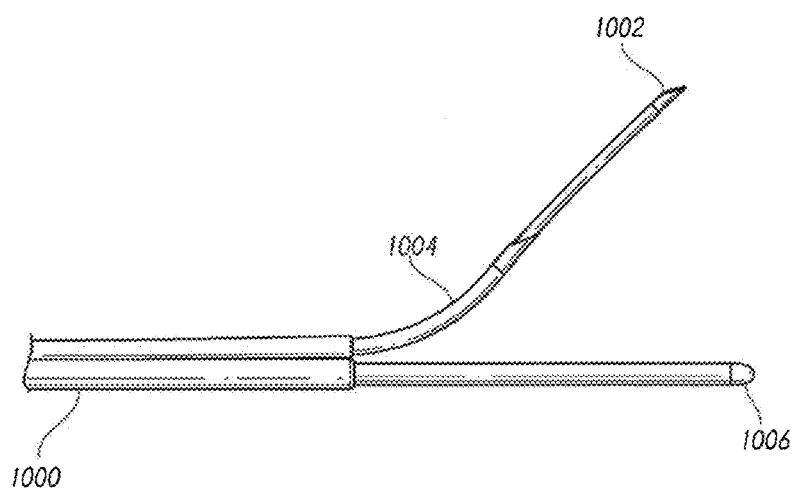

FIGS. 14A-B illustrate an embodiment of a flexible needle 1002 inserted into a multi-lumen, steerable catheter 1000 similar to FIG. 11C. The probe 1006 may be a miniaturized ultrasound probe, and is preferably inserted into one of the catheter lumens. In FIG. 14A, the flexible needle 1002 is shown in a retracted configuration and is inside a sheath 1004. FIG. 14B shows the flexible needle 1002 in an extended position and articulated. The needle 1002 may be articulated, for example, using the steering wires described above in relation to the embodiment in FIG. 11C. Here, the needle can achieve an articulation of approximately 20 degrees relative to the distal end of the probe 1006.

Figure 15A:
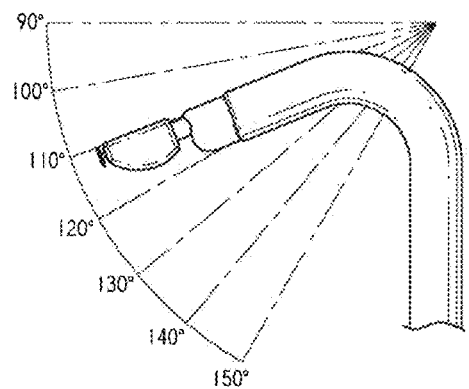
FIGS. 15A-C are illustrations of a bronchoscope comprising an ultrasound probe and showing various degrees of articulation achievable without any biopsy needle, with a conventional straight biopsy needle, and with an embodiment of a flexible biopsy needle.
Figure 15B:
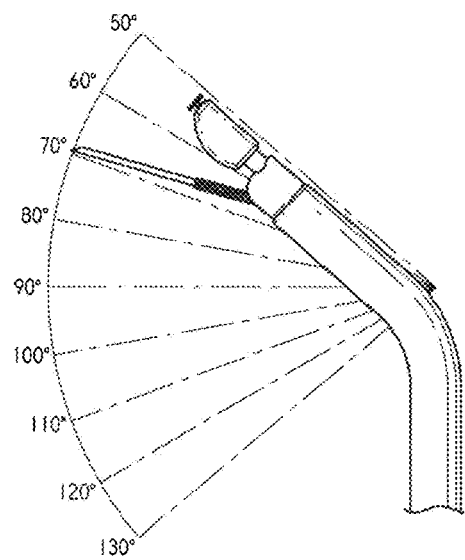
Figure 15C:
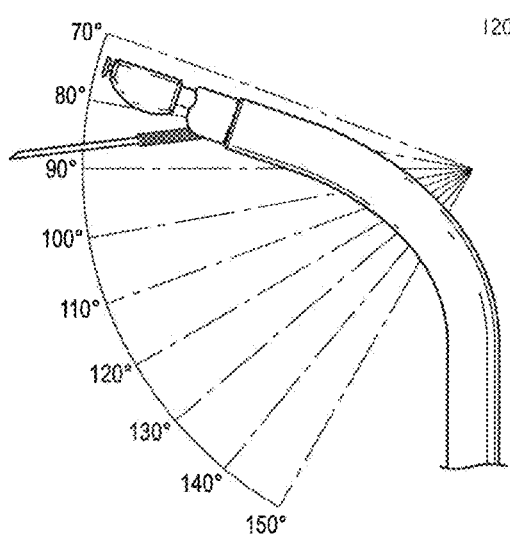

FIGS. 15A-C illustrate various states of articulation of a bronchoscope comprising an ultrasound probe similar to that illustrated in FIG. 1. First, FIG. 15A shows the articulation of the bronchoscope without any biopsy needle inserted therein. The bronchoscope can achieve an articulation of approximately 110 degrees. FIG. 15B shows the bronchoscope with a conventional straight biopsy needle and catheter inserted therein. The bronchoscope's articulation is reduced to approximately 50 degrees, with the straight needle providing approximately 20 degrees of additional angle (for a total of 70 degrees). FIG. 15C shows the same bronchoscope with a flexible needle and catheter inserted therein similar to the embodiment illustrated in FIG. 2. Here, the bronchoscope can bend to approximately 90 degrees, with the flexible needle providing approximately additional 20 degrees of additional angle (for a total of 110 degrees). It is important to note that the flexible needle illustrated in FIG. 15C is not being articulated independently of the bronchoscope, and an additional independent articulation mechanism (including for example but without limitation the embodiments illustrated in FIGS. 6A-D and/or FIG. 8)

can provide for additional angulation and articulation of the needle to permit access to tortuous spaces.

Figures 16A, 16B:
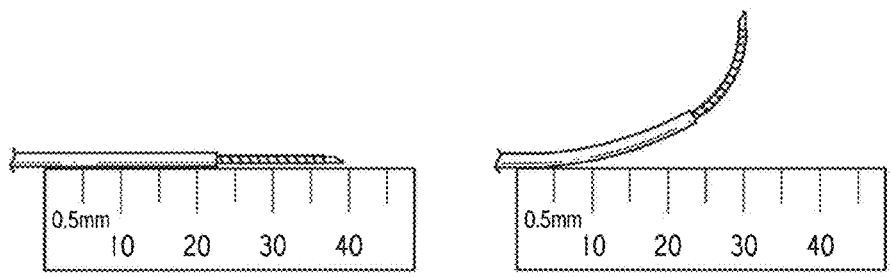
FIGS. 16A-C are illustrations of an embodiment of a flexible needle.
Figure 16C:
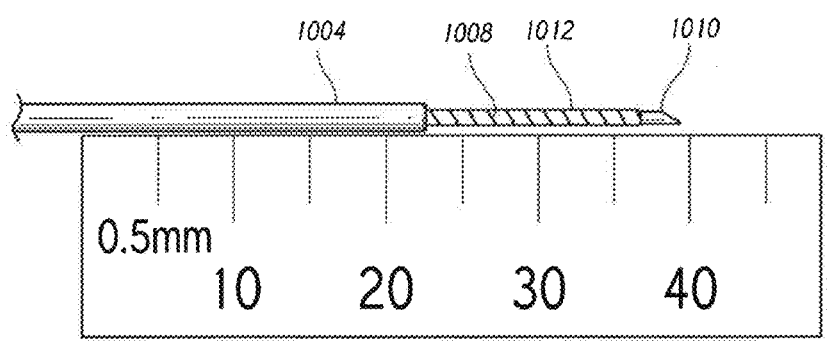

FIGS. 16A-C illustrate another embodiment of a flexible needle and catheter, of which the needle may be similar to the embodiment illustrated in FIG. 2. FIGS. 16A-B depict the articulation of the needle independent of any steering mechanism, and show that the needle can bend approximately 90 degrees. FIG. 16C is a close up of the flexible needle 1002, and illustrates a needle sheath or catheter 1004 covering the more proximal section of the flexible needle 1002. The flexible needle 1002 extends past the distal end of the sheath 1004, and has a flexible section 1008 (similar to the flexible shaft portion 204 discussed above) that includes spiral "jigsaw" cuts covered with a layer of heat shrink material. The extreme distal tip 1010 of the flexible needle is uncovered and lacks cuts, and is sharpened so as to pierce into tissue.

Figure 17:
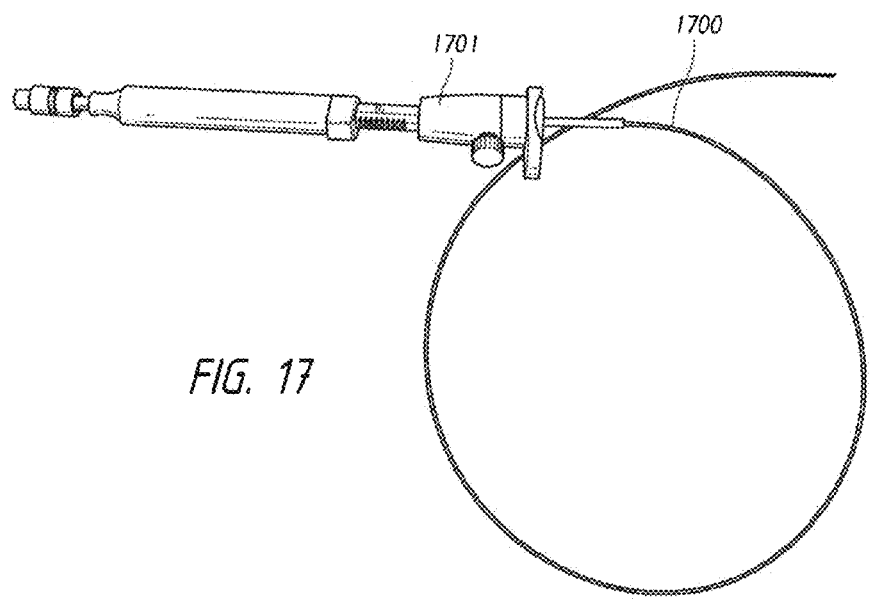
FIG. 17 is an illustration of a handle that may be used to manipulate and control embodiments of the flexible needles described herein.

FIG. 17 illustrates a handle 1701 that may be used to manipulate and control embodiments of the flexible needles described herein. The handle 1701 is connected to a catheter 1700 with a flexible needle hypotube within, and the handle 1701 can control the extension of the needle from the catheter.

Figure 18:
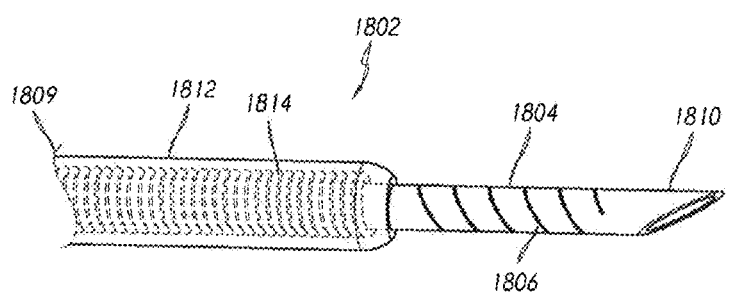
FIG. 18 is an illustration of an embodiment of a flexible needle showing the distal tip thereof.

FIG. 18 is a close-up view of an embodiment of a flexible needle 1802. This embodiment has a flexible section 1804 comprising a spiral cut 1806, and which extends close to the extreme distal tip 1810 of the flexible needle 1802. The distal tip 1810 is preferably beveled and sharpened so as to penetrate into tissue. The proximal end 1809 of the flexible needle may be optionally covered by a polymeric sheath 1812 with coils 1814 underneath and overlying the body of the flexible needle 1802. Preferably, the coils 1814 provide structural support to the needle 1802 to reduce or eliminate the likelihood that the needle 1802 will prolapse or collapse, in particular when the needle 1802 is bent or articulated.

Figure 19:
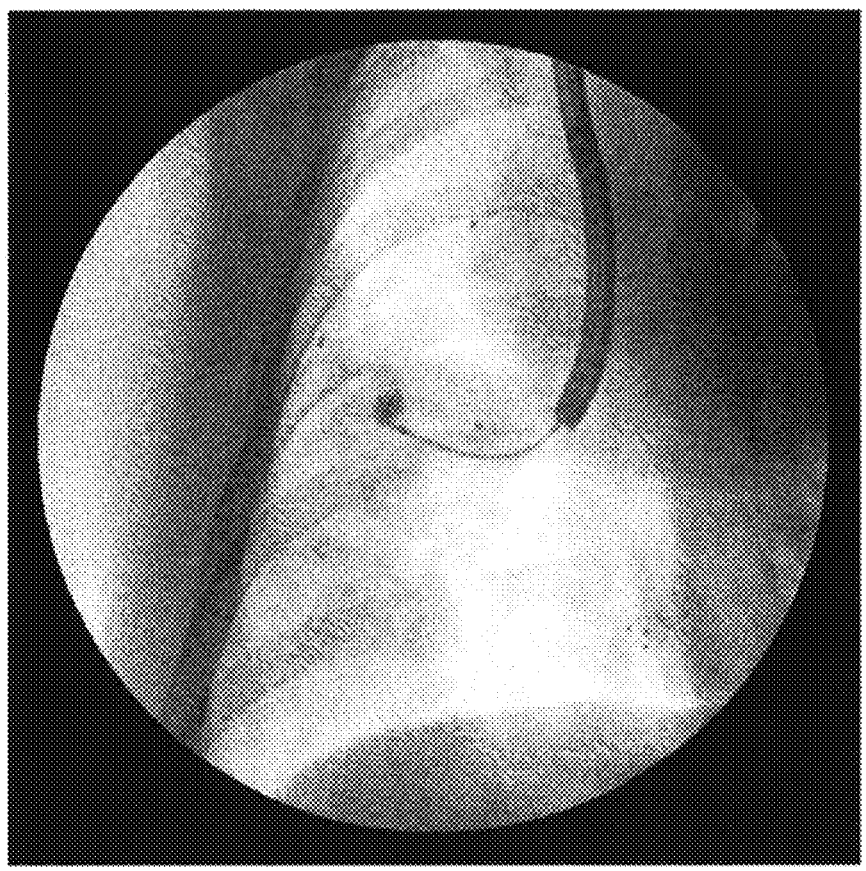
FIG. 19 is a fluoroscopy image of an embodiment of a flexible needle with an inner guidewire.

FIG. 19 is a fluoroscopy image similar to that illustrated in FIG. 10. Here, a bronchoscope of the right side of the image has a catheter extending from it. The catheter includes a coil at its distal end that may aid visualization of the device. A flexible needle also extends from the distal end of the catheter and is depicted here piercing into and biopsying a lung nodule (the darker circular object on the left). The flexible needle is guided by an inner guidewire similar to the embodiment illustrated in FIG. 8.

It will be understood that the present descriptions of the lung biopsy systems, apparatuses, and methods described herein as being used in a lung and for lung nodules are not limiting, and that these embodiments may be used for biopsying, navigating, and locating areas of interest in other locations on a patient, including gastric, endoscopic, or other suitable locations. Similarly, a bronchoscope is not necessary, and other suitable devices capable of accommodating the embodiments described herein may also be used, including without limitation various endoscopes or laparoscopic cannulas.

Figure 20A:
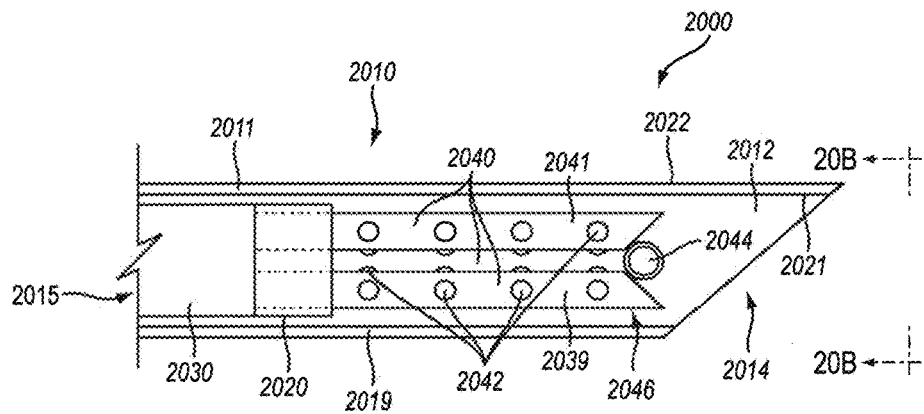
FIG. 20A is a partial cross-section view of a delivery needle in which one or more internal needles are positioned.

As illustrated in FIG. 20A, a substance delivery system 2000 can include a delivery needle 2010. In some embodiments, the delivery needle 2010 can be similar to or the same as the flexible TBNA needles described herein. The delivery needle 2010 can be hollow. In some embodiments, the delivery needle 2010 defines a delivery lumen 2012 and has a delivery needle wall 2019. The delivery needle wall has an internal surface 2021 and an outside surface 2022. The delivery lumen 2012 can extend through the distal end 2014 of the delivery needle 2010. In some embodiments, the delivery lumen 2012 extends through the entire length of the delivery needle 2010. The delivery needle 2010 can include a solid (e.g., without an internal lumen) portion (not shown) at and/or near a proximal end of the delivery needle 2010. In some embodiments, the distal end 2014 of the delivery needle 2010 can be configured to pierce tissue within the body. For example, the delivery needle 2010 can be beveled or otherwise sharpened at its distal end 2014. The delivery needle 2010 can be navigated to a site of interest (e.g., a nodule, lesion, or other site of interest) within the body via the working channel of a delivery device (e.g., a bronchoscope, endoscope). In some embodiments, the delivery needle 2010 is navigated to the site of interest using a catheter. The delivery needle 2010 can be positioned within a sheath to protect the distal end 2014 and/or the working channel of the delivery device or catheter from damage. The sheath can be retracted from the delivery needle 2010 prior to deploying the needle 2010 to the site of interest. In some embodiments, the delivery needle 2010 can be advanced distally past the distal end of the sheath in a manner similar to the needles described above.

In some embodiments, at least a portion of the length of the delivery needle 2010 is flexible. For example, delivery needle 2010 can include flexibility increasing features similar to or the same as those described with respect to the flexible and/or transbronchial needles above. Such flexibility increasing features can include cuts in the wall 2011 of the delivery needle 2010. In some embodiments, one or more cut patterns can be cut into portions of the wall 2011 of the delivery needle 2010. For example, jigsaw cuts, straight cuts, spiral cuts, interrupted spiral cuts, partial or dashed cuts, zigzag cuts, sinusoidal cuts, and/or any combination of these or similar cuts would be made in a portion of or along the entire length of the wall 2011 of the delivery needle 2010.

According to some variants, the wall 2011 of the delivery needle 2010 is coated. For example, the interior surface and/or exterior surface of the wall 2011 can include a heat shrink material or some other coating. The coating can be configured to reduce or eliminate the likelihood that fluid would leak through the wall 2011 between the delivery lumen 2012 and the surroundings of the lumen 2012.

Figure 20B:
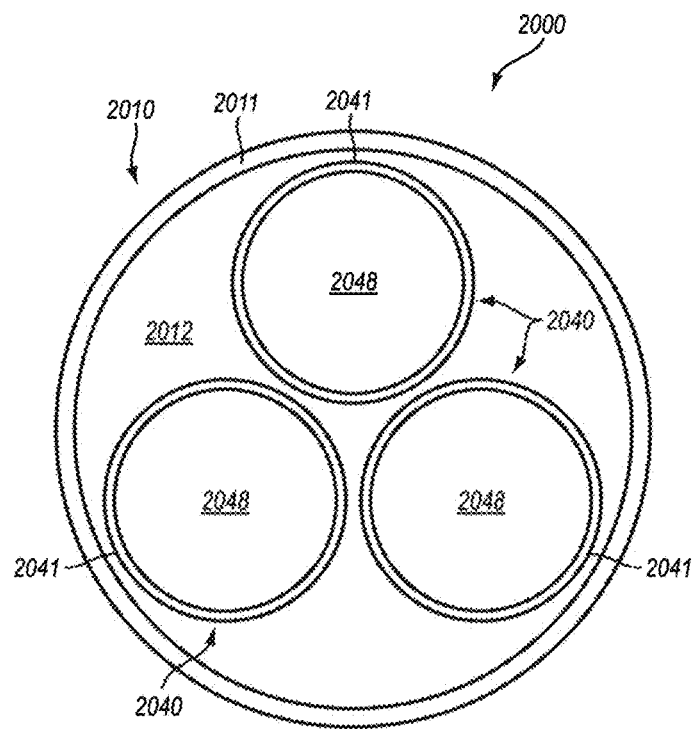
FIG. 20B is an elevated end view of the delivery needle of FIG. 20A from the viewing plane 20B-20B of FIG. 20A.

As illustrated in FIGS. 20A-20B, one or more internal flexible needles 2040 can be positioned within the delivery needle 2010. For example, the internal flexible needles 2040 can be sized (e.g., have diameters) such that three internal needles 2040 can be stored within the delivery needle 2010. Many variations in the number of needles 2040 configured to fit within the delivery needle 2010 are possible (e.g., 2 needles, 4 needles, 6 needles).

In some embodiments, the internal needles 2040 extend the length of the delivery needle 2010 (e.g., from the proximal end of the delivery needle 2010 to the distal end 2014 of the delivery needle 2010). Preferably, the internal needles 2040 can be attached to a flexible shaft 2030. The flexible shaft 2030 can comprise a tube comprise a polymer tube, a metallic or polymer coil, and/or a laser or chemical cut hypotube. In some embodiments, the internal needles 2040 are attached to the distal end of the flexible shaft 2030 via a collar 2020. The collar 2020 can be, for example, an adhesive binding. In some embodiments, the collar 2020 can be constructed from a metallic material onto which the interior needles 2040 can be welded or otherwise adhered. In some embodiments, the internal needles 2040 are coupled with the flexible shaft 2030 directly, without the use of a collar 2020.

As illustrated in FIG. 20B, the internal needles 2040 can be hollow and can define internal needle lumens 2048. The internal needle lumens 2048 can be in fluid communication with an interior lumen of the flexible shaft 2030. In some embodiments, the proximal ends of the flexible shaft 2030, the internal lumen 2012, and/or internal needle lumens 2048 are in fluid communication with a delivery fluid source. For example, the internal needle lumens 2048 can be in fluid communication with an external fluid source (e.g., a syringe, a peristaltic pump), either directly or via the interior lumen of the flexible shaft 2030.

The flexible shaft 2030 and/or internal needles 2040 can be configured to move in the distal and/or proximal directions with respect to the delivery needle 2010. For example, the internal needles 2040 can be connected to a proximal handle (not shown), either directly or via the flexible shaft 2030. The proximal handle can be configured to move the flexible shaft 2030 and/or internal needles 2040 in the proximal and distal directions with respect to the delivery needle 2010. In some embodiments, a first proximal handle can be connected to the flexible shaft 2030 and a second proximal handle can be connected to the internal needles 2040. In some embodiments, the internal needles 2040 can be moved in the proximal and distal directions with respect to the flexible shaft 2030 and/or the collar 2020. In some embodiments, each of the internal needles 2040 can be individually (or, e.g., in subsets of the whole set of internal needles 2040) connected to a proximal handle. In some such embodiments, each (e.g., or each subset) of the internal needles 2040 can be moved in the distal and proximal directions with respect to the other internal needles 2040.

The internal needles 2040 can be constructed from a metal or metal alloy, such as stainless steel, steel, titanium, or some other appropriate material. In some embodiments, the internal needles 2040, or some portion thereof, are constructed from a polymer or other non-metallic material. Preferably, at least a portion of each of the internal needles 2040 is constructed from nitinol or some other shape-memory material.

Figure 21A:
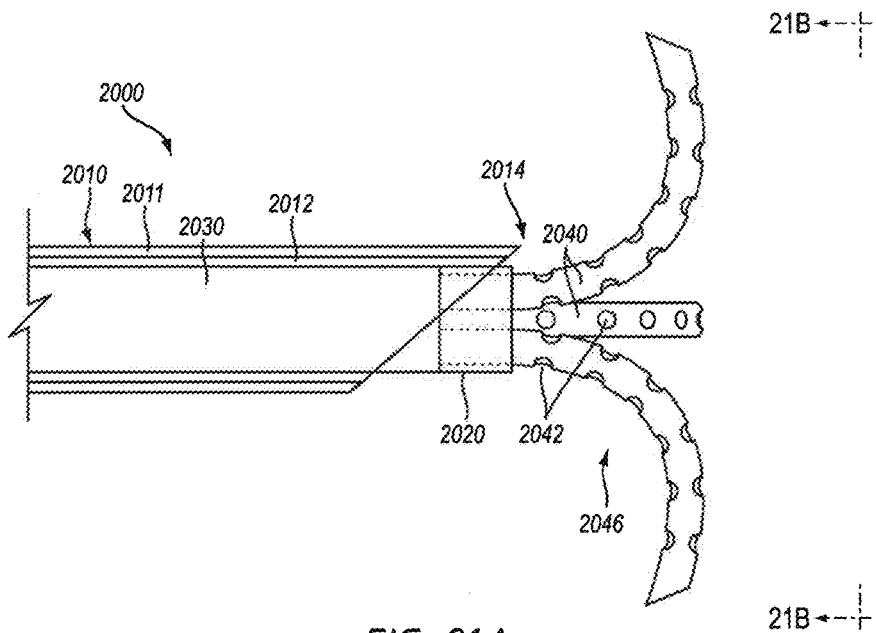
FIG. 21A is a partial cross-section view of the delivery needle of FIG. 20A wherein the one or more internal needles are deployed outside of the delivery needle.
Figure 21B:
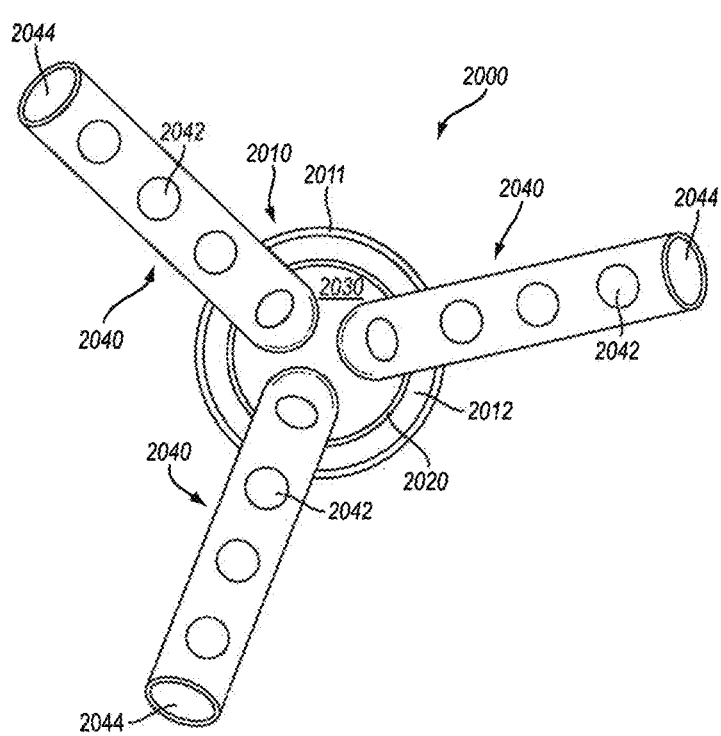
FIG. 21B is an elevated end view of the delivery needle and one or more deployed internal needles of FIG. 21A from the viewing plane 21B-21B of FIG. 21A.

In some embodiments, the internal needles 2040 are configured to transition between a contracted position (e.g., as illustrated in FIGS. 20A-20B) and an expanded position (e.g., as illustrated in FIGS. 21A-21B). In the expanded position, the internal needles 2040 can flare out from the distal end 2014 of the delivery needle 2010. In some embodiments, the internal needles 2040 transition from the contracted position to the expanded position as the distal ends 2046 of the internal needles 2040 pass the distal end 2014 of the delivery needle 2010. In some embodiments, the wall 2011 of the delivery needle 2010 includes one or more apertures through which the internal needles 2040 can pass when transitioning between the contracted position and the expanded position. The extent to which the internal needles 2040 flare out from the distal end 2014 of the delivery needle 2010 can, in some embodiments, be controlled by the relative distal movement of the internal needles 2040 relative to the delivery needle 2010. For example, once past the distal end 2014 of the delivery needle 3010 (or, e.g., through the apertures in the wall 2011 of the delivery needle 2010), the distal ends 2046 of the internal needles 2040 can be configured to flare out further from the delivery needle 2010 as the flexible shaft 2030 and/or internal needles 2040 are advanced in the distal direction relative to the delivery needle 2010. The interior surface of the wall 2011 of the delivery needle 2010 can include a coating to reduce or eliminate the likelihood that the internal needles 2040 would catch on the interior surface of the wall 2011 as the internal needles 2040 translate in the proximal and/or distal directions with respect to the delivery needle 2010.

The internal needle lumen 2039, having walls 2041, of the internal needles 2040 can include cut (e.g., laser cut and/or chemical cut) features 2042 such as, for example, holes or slits. The cut features 2042 can facilitate fluid communication between the internal needle lumens 2048 and the tissue into which the internal needles 2040 are deployed. The cut features 2042 can be placed on the sides of the internal needles 2040 that are compressed and stretched as the needles 2040 deploy from the distal end 2014 of the delivery needle 2010. In some embodiments, the cut features 2042 are made into the sides of the needles 2040 tangential to the direction of bending as the needles 2040 extend from the distal end 2014 of the delivery needle 2010 (e.g., as illustrated in FIG. 21A). According to some variants, the cut features 2042 are located at various points around the wall of the needles 2040. In some embodiments, the distal ends 2046 of the internal needles 2040 include distal apertures 2044 at a distal end 2045 in fluid communication with the internal needle lumens 2048 of the internal needles 2040.

The internal needles 2040 and/or delivery needle 2010 can be configured (via, e.g., cut features and/or cut patterns in the walls 2041, 2011 of the needles 2040, 2010) to be flexible such that the delivery needle 2010 can be navigated to and/or through narrow and/or tortuous lumens within the body. As such, the substance delivery system 2000 can be delivered to a site of interest within the body using the body's natural orifices (e.g., the mouth). In some embodiments, piercing of tissue within the body (other than piercing an airway wall to access extrinsic areas of interest outside of the airway) can be avoided by using a flexible substance delivery system 2000 as described. According to some variants, the delivery needle 2010 and internal needles 2040 can be navigated to the site of interest (e.g., nodule, tumor, lesion) to be treated using a bronchoscope of other delivery device. For example, the delivery needle 2010 can be delivered to a site of interest in the lung via a bronchoscope inserted through the airways of the throat and lung. In some embodiments, the delivery needle 2010 is navigated to the site of interest thoracoscopically (e.g., through an incision in torso of the patient). In some embodiments, the delivery needle 2010 can be navigated to the site of interest using a delivery catheter similar to or the same as the delivery catheter 1100 described above with respect to FIG. 11C. For example, an ultrasound probe 1116 can be used to navigate the delivery needle 2010 to the site of the interest. The ultrasound probe 1116 can facilitate real-time tracking of the needle 2010 as the needle 2010 is navigated to the site of interest.

Figure 22A:
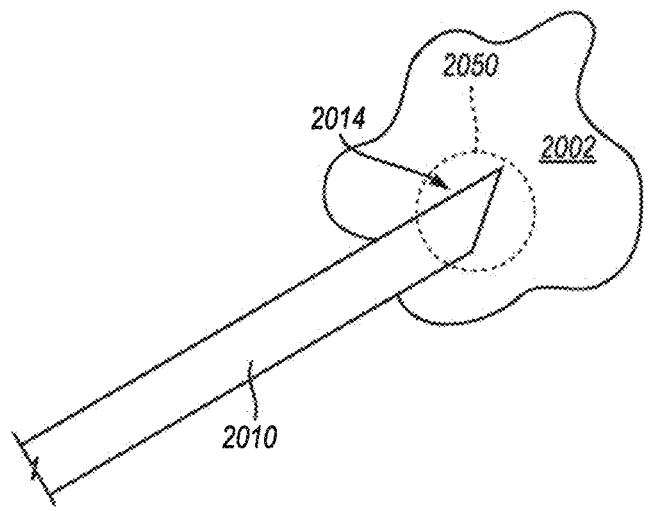
FIG. 22A illustrates a delivery needle in communication with an area of interest within the body.

FIG. 22A illustrates an embodiment of a delivery needle 2010 used to treat an area of interest 2002 (e.g., a nodule, tumor, lesion). Used alone, a delivery needle 2010 (or other single-lumen needle) can have zone of efficacy 2050 within and/or around the area of interest 2002. For example, the delivery needle 2010 can be delivered to the area of interest 2002 and be inserted (e.g., piercably) into the area of interest 2002. A syringe or other fluid source (not shown) can be connected to the proximal end 2015 of the delivery needle 2010 and can be used to introduce a treatment substance (e.g., an ablative chemical solution) to the area of interest 2002 through the needle 2010. The treatment substance can travel through the distal end 2014 of the needle 2010 to affect a zone of efficacy 2050. The zone of efficacy 2050 can generally comprise the area treated or otherwise affected by the treatment substance.

Figure 22B:
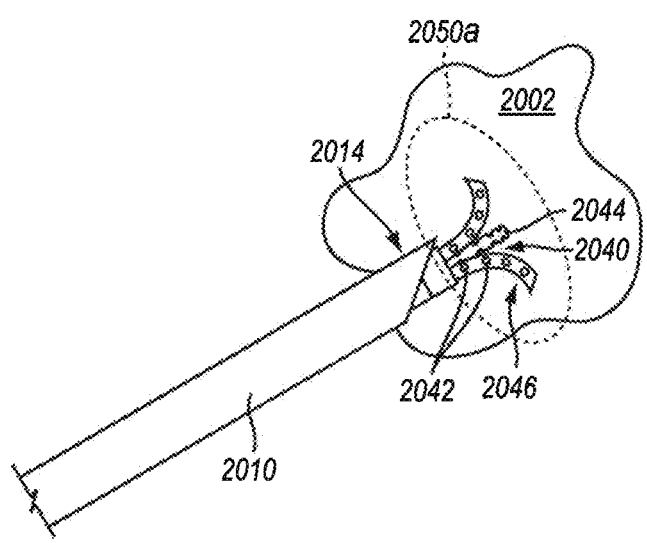
FIG. 22B illustrates a delivery needle with deployed internal flexible needles in communication with an area of interest within the body.
Figure 23A:
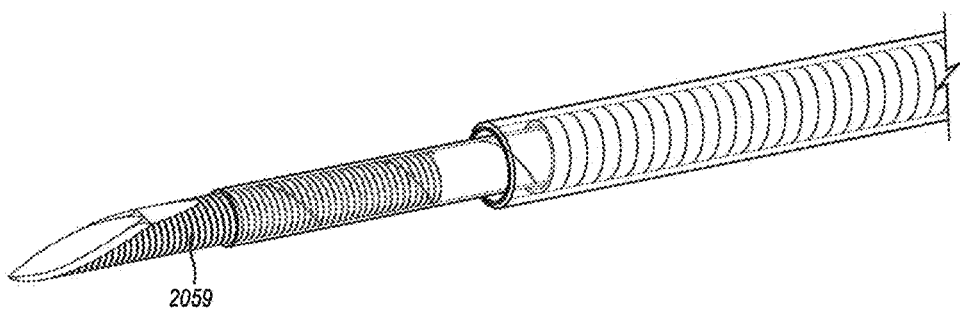
FIG. 23A illustrates an isometric view of a delivery needle with a spiral scribe on the distal tip, which may be used to reflect ultrasound waves.
Figure 23B:
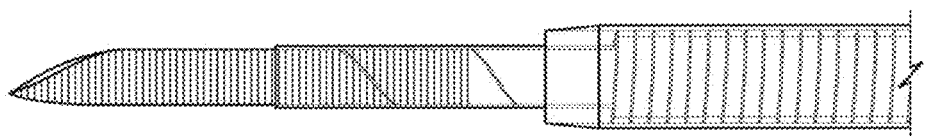
FIG. 23B illustrates a side view of a delivery needle with a spiral scribe on the distal tip, which may be used to reflect ultrasound waves.

As illustrated in FIG. 22B, the use of multiple internal needles 2040 can increase the size of the zone of efficacy 2050a compared to the zone of efficacy 2050 realized using a single-lumen, single needle treatment approach. For example, the delivery needle 2010 can be navigated to the area of interest 2002. The distal end 2014 of the delivery needle 2010 can be inserted (e.g., piercably) into the site of interest 2002. The internal needles 2040 can be moved distally with respect to the distal end 2014 of the delivery needle 2010 to further penetrate the site of interest 2002. As described above, the internal needles 2040 can be configured to flare outward from the distal end 2014 of the delivery needle 2010 as the internal needles 2040 are advanced out of the delivery needle 2010 in the distal direction. A syringe or other fluid source can be connected to the proximal end of the internal needles 2040 and/or flexible tube 2030 and can be used to introduce a treatment substance (e.g., an ablative chemical solution) to the area of interest 2002 through the internal needles 2040. In some embodiments, the treatment substance is ethanol, which can be used to treat and/or destroy tumors. The treatment substance can travel through the cut features 2042 and/or distal aperture 2044 to disperse the treatment substance and create a zone of efficacy 2050*a* that can be greater in size than the zone of efficacy 2050 realized using a single lumen, single needle treatment approach.

Various example embodiments of the disclosure can be described in view of the following clauses:

Clause 1: A system includes a bronchoscope comprising an insertion tube having a working channel and a catheter configured to be received within the working channel. The catheter includes a first lumen extending from a proximal end of the catheter to a distal end of the catheter and a second lumen extending from the proximal end of the catheter to a distal end of the catheter. The system also includes an ultrasound probe slidably received within the first lumen and a tissue sampling device slidably received within the second lumen.

Clause 2: The system of Clause 1, wherein the catheter further includes a mechanism for adjusting the angle of the distal tip of at least one of the first lumen, the second lumen or the tissue sampling device.

Clause 3: The system of Clause 2, wherein the mechanism includes one or more steering wires.

Clause 4: The system of Clause 3, wherein the one or more steering wires includes a Bowden wire.

Clause 5: The system of Clause 1, wherein the ultrasound probe includes a radial ultrasound probe that generates at least one real-time ultrasound image of at least one of the tissue sampling device or surrounding tissue.

Clause 6: The system of Clause 1, wherein the tissue sampling device includes a biopsy needle.

Clause 7: The system of Clause 1, wherein the working channel is at most a 3.2 mm diameter working channel.

Clause 8: The system of Clause 1, wherein the tissue sampling device includes a lumen extending from a proximal end of the catheter to a distal end of the tissue sampling device, further comprising a guidewire received within the lumen of the tissue sampling device.

Clause 9: The system of Clause 8, wherein the guidewire includes a shape memory material.

Clause 10: The system of Clause 9, wherein the guidewire includes a portion being set in a curved configuration, wherein the tissue sampling device includes a flexible section, wherein when the portion of the guidewire is received within the flexible section, the flexible section of the tissue sampling device bends away from a longitudinal axis of the catheter.

Clause 11: A method includes inserting a portion of an insertion tube into the lumen of a specimen and inserting a catheter into a working channel of a bronchoscope. The catheter includes a first lumen extending from a proximal end of the catheter to a distal end of the catheter and a second lumen extending from the proximal end of the catheter to the distal end of the catheter. The method further includes inserting an ultrasound probe into the first lumen until at least a portion of the probe extends beyond the distal end of the catheter and inserting a tissue sampling device into the second lumen until at least a portion of the tissue sampling device extends beyond the distal end of the catheter.

Clause 12: The method of Clause 11, wherein the catheter further includes a mechanism for adjusting the angle of the distal tip of at least one of the first lumen, the second lumen or the tissue sampling device, further comprising manipulating a position of at least one of the first lumen, the second lumen or the tissue sampling device using the mechanism.

Clause 13: The method of Clause 12, wherein the mechanism includes one or more steering wires.

Clause 14: The method of claim 13, wherein the one or more steering wires includes a Bowden wire.

Clause 15: The method of Clause 11, further comprising generating at least one real-time ultrasound image of at least one of the tissue sampling device or surrounding tissue using the ultrasound probe, wherein the ultrasound probe includes a radial ultrasound probe.

Clause 16: The method of Clause 11, wherein the tissue sampling device includes a biopsy needle.

Clause 17: The method of Clause 11, wherein the working channel is at most a 3.2 mm diameter working channel.

Clause 18: The method of Clause 11, wherein the tissue sampling device includes a lumen extending from a proximal end of the catheter to a distal end of the tissue sampling device, further comprising receiving a guidewire within the lumen of the tissue sampling device.

Clause 19: The method of Clause 18, wherein the guidewire includes a shape memory material.

Clause 20: The method of Clause 19, further comprising: setting a portion of the guidewire in a curved configuration, wherein the tissue sampling device includes a flexible section; and bending the flexible section of the tissue sampling device away from a longitudinal axis of the catheter, when the portion of the guidewire is received within the flexible section.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:

1. A system comprising:
a bronchoscope comprising an insertion tube having a working channel;

a catheter configured to be received within the working channel, the catheter comprising:
  a first lumen extending from a proximal end of the catheter to a distal end of the catheter; and
  a second lumen extending from the proximal end of the catheter to the distal end of the catheter;
an ultrasound probe slidably received within the first lumen; and
a tissue sampling device slidably received within the second lumen,
  wherein the tissue sampling device comprises a lumen extending from the proximal end of the catheter to a distal end of the tissue sampling device, further comprising a guidewire received within the lumen of the tissue sampling device,
  wherein the guidewire comprises a shape memory material; and
  wherein the guidewire comprises a portion being set in a curved configuration,
wherein the tissue sampling device comprises a flexible section, wherein when the portion of the guidewire is received within the flexible section, the flexible section of the tissue sampling device bends away from a longitudinal axis of the catheter.

2. The system of claim 1, wherein the catheter further comprises a mechanism for adjusting the angle of the distal tip of at least one of the first lumen, the second lumen or the tissue sampling device.

3. The system of claim 2, wherein the mechanism comprises one or more steering wires.

4. The system of claim 3, wherein the one or more steering wires comprises a Bowden wire.

5. The system of claim 1, wherein the ultrasound probe comprises a radial ultrasound probe that generates at least one real-time ultrasound image of at least one of the tissue sampling device or surrounding tissue.

6. The system of claim 1, wherein the tissue sampling device comprises a biopsy needle.

7. The system of claim 1, wherein the working channel is at most a 3.2 mm diameter working channel.

8. A method comprising:
  inserting a portion of an insertion tube into the lumen of a specimen;
  inserting a catheter into a working channel of a bronchoscope, wherein the catheter comprises:
    a first lumen extending from a proximal end of the catheter to a distal end of the catheter; and
    a second lumen extending from the proximal end of the catheter to the distal end of the catheter;
  inserting an ultrasound probe into the first lumen until at least a portion of the probe extends beyond the distal end of the catheter; and
  inserting a tissue sampling device into the second lumen until at least a portion of the tissue sampling device extends beyond the distal end of the catheter;
  wherein the tissue sampling device comprises a lumen extending from a proximal end of the catheter to a distal end of the tissue sampling device, further comprising receiving a guidewire within the lumen of the tissue sampling device,
  wherein the guidewire comprises a shape memory material; and
  setting a portion of the guidewire in a curved configuration, wherein the tissue sampling device comprises a flexible section; and
  bending the flexible section of the tissue sampling device away from a longitudinal axis of the catheter, when the portion of the guidewire is received within the flexible section.

9. The method of claim 8, wherein the catheter further comprises a mechanism for adjusting the angle of the distal tip of at least one of the first lumen, the second lumen or the tissue sampling device, further comprising manipulating a position of at least one of the first lumen, the second lumen or the tissue sampling device using the mechanism.

10. The method of claim 9, wherein the mechanism comprises one or more steering wires.

11. The method of claim 10, wherein the one or more steering wires comprises a Bowden wire.

12. The method of claim 8, further comprising generating at least one real-time ultrasound image of at least one of the tissue sampling device or surrounding tissue using the ultrasound probe, wherein the ultrasound probe comprises a radial ultrasound probe.

13. The method of claim 8, wherein the tissue sampling device comprises a biopsy needle.

14. The method of claim 8, wherein the working channel is at most a 3.2 mm diameter working channel.

* * * * *